(12) United States Patent
Tomooka et al.

(10) Patent No.: US 11,603,337 B2
(45) Date of Patent: Mar. 14, 2023

(54) METHOD FOR PRODUCING OPTICALLY ACTIVE SUBSTANCE, OPTICALLY ACTIVE SUBSTANCE, METHOD FOR PRODUCING CHIRAL MOLECULE, AND CHIRAL MOLECULE

(71) Applicants: KYUSHU UNIVERSITY, NATIONAL UNIVERSITY CORPORATION, Fukuoka (JP); DAICEL CORPORATION, Osaka (JP)

(72) Inventors: Katsuhiko Tomooka, Fukuoka (JP); Kazunobu Igawa, Fukuoka (JP)

(73) Assignees: DAICEL CORPORATION, Osaka (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 16/614,009

(22) PCT Filed: May 16, 2018

(86) PCT No.: PCT/JP2018/018865
§ 371 (c)(1),
(2) Date: Nov. 15, 2019

(87) PCT Pub. No.: WO2018/212216
PCT Pub. Date: Nov. 22, 2018

(65) Prior Publication Data
US 2020/0087227 A1 Mar. 19, 2020

(30) Foreign Application Priority Data

May 17, 2017 (JP) .............................. JP2017-097928

(51) Int. Cl.
| | |
|---|---|
| *C07B 57/00* | (2006.01) |
| *C07C 311/20* | (2006.01) |
| *C07D 491/044* | (2006.01) |
| *C07C 231/20* | (2006.01) |
| *C07C 233/88* | (2006.01) |
| *C07C 235/40* | (2006.01) |
| *C07C 303/40* | (2006.01) |
| *C07F 7/18* | (2006.01) |

(52) U.S. Cl.
CPC ............ *C07B 57/00* (2013.01); *C07C 231/20* (2013.01); *C07C 233/88* (2013.01); *C07C 235/40* (2013.01); *C07C 303/40* (2013.01); *C07C 311/20* (2013.01); *C07F 7/18* (2013.01); *C07D 491/044* (2013.01)

(58) Field of Classification Search
CPC ...... C07B 57/00; C07C 11/20; C07D 491/044
See application file for complete search history.

(56) References Cited

FOREIGN PATENT DOCUMENTS

JP 2005-255658 A 9/2005

OTHER PUBLICATIONS

Jung. Organic Letters, 2000, 2 (17), 2659-2661, supporting information pp. 1-14 (Year: 2000).*
Tomooka. Journal of the American Chemical Society, 2005, 127, 12182-12183, supporting information S1-S8 (Year: 2006).*
Benedekovic. Bioorganic and Medicinal Chemistry Letters, 2016, 26, 3318-21. (Year: 2016).*
Merlani. Chirality, 2010, 22, 717-725 (Year: 2010).*
Bringmann et al., "Atropisomerization Barriers of Configurationally Unstable Biaryl Compounds, Useful Substrates for Atroposelective Conversions to Axially Chiral Biaryls", J. Org. Chem., vol. 65, pp. 722-728.
Extended European Search Report dated Dec. 15, 2020, in European Patent Application No. 18802791.6.
Chinese Office Action and Search Report for Chinese Application No. 201880032166.8, dated Jan. 20, 2022, with an English translation.
Bringmann et al., "Atropisomerization Barriers of Configurationally Unstable Biaryl Compounds, Useful Substrates for Atroposelective Conversions to Axially Chiral Biaryls", J. Org. Chem., vol. 65, pp. 722-728. 2000.
International Preliminary Report on Patentability and English translation of the Written Opinion of the International Searching Authority dated Nov. 19, 2019 for Application No. PCT/JP2018/018865.
International Search Report and Written Opinion of the International Searching Authority dated Aug. 21, 2018 for Application No. PCT/JP2018/018865.
Office Action issued in Chinese Patent Application No. 201880032166.8, dated Jan. 20, 2023.

* cited by examiner

*Primary Examiner* — Noble E Jarrell
(74) *Attorney, Agent, or Firm* — Birch, Stewart, Kolasch & Birch, LLP

(57) ABSTRACT

Provided is a method for producing an optically active substance, the method including an asymmetric induction, wherein an asymmetry inducer is allowed to act on a chiral molecule having a half-life of enantiomeric excess of shorter than 10 hours, thereby increasing abundance of one enantiomer of the chiral molecule. According to this method, one enantiomer of a chiral molecule that is susceptible to racemization can be selectively and efficiently obtained.

10 Claims, No Drawings

METHOD FOR PRODUCING OPTICALLY ACTIVE SUBSTANCE, OPTICALLY ACTIVE SUBSTANCE, METHOD FOR PRODUCING CHIRAL MOLECULE, AND CHIRAL MOLECULE

TECHNICAL FIELD

The present invention relates to a method for selectively obtaining one enantiomer of a chiral molecule whose enantiomers interconvert rapidly (hereinafter, a dynamically chiral molecule), and a method utilizing such a method to further produce a chiral molecule whose enantiomers do not interconvert (hereinafter, a statically chiral molecule) or a chiral molecule whose enantiomers interconvert more slowly than those of a dynamically chiral molecule (hereinafter, a quasi-statically chiral molecule).

BACKGROUND ART

Chiral molecules include a pair of enantiomers (mirror image isomers). Although those enantiomers have the same general chemical and physical properties, but the sign of optical rotation is reversed, and the physiological activity is greatly different. Thus, the selective use of only one of the enantiomers is extremely important for the development of pharmaceuticals and functional materials. Accordingly, an enormous amount of research has been conducted on methods for selectively obtaining one enantiomer to date.

Chiral molecules include, for example, a chiral carbon molecule having an $sp^3$ carbon atom as an asymmetric center, which is known as a representative example. Here, one enantiomer of a chiral carbon molecule and the other enantiomer have different stereo configurations around the asymmetric carbon. Therefore, to obtain only one enantiomer by converting the other enantiomer of a racemic modification to the one enantiomer, cleavage and reformation of a bond to the asymmetric carbon, which requires an extremely high energy, are indispensable. Thus, methods for selectively obtaining one enantiomer of a chiral carbon molecule that do not involving such an interconversion are mainly used. Such methods include an optical resolution method and an asymmetric synthesis method. The optical resolution method separates only one enantiomer from a racemic modification (a mixture containing a pair of enantiomers at a ratio of 50:50) that is readily available, and the asymmetric synthesis method uses an achiral molecule as a production raw material (substrate) in an enantioselective reaction to selectively synthesize one enantiomer (for example, see Non-Patent Document 1).

CITATION LIST

Non-Patent Document

Non-Patent Document 1: "Asymmetric Synthesis", edited by James D. Morrison, published by Academic Press (New York), 1983

SUMMARY OF INVENTION

Technical Problem

However, the optical resolution method separates the enantiomer from the racemic modification, and thus the yield of the target enantiomer is at most only 50%, and at least half of the chiral molecule is wasted. In addition, the asymmetric synthesis method needs to use a special chiral reagent for enantioselectively reaction of the substrate, thus has many restrictions on the applicable chiral molecules and lacks versatility.

Thus, to solve such problems of the related art, the present inventors have investigated to provide a method that can selectively and efficiently provide one enantiomer of a chiral molecule even without using a chiral reagent.

Solution to Problem

As a result of diligent research to solve the above problems, the present inventors have found that if an asymmetry inducer is allowed to act at room temperature on a dynamically chiral molecule having a half-life of enantiomeric excess of shorter than 10 hours at 50° C., the other enantiomer of the chiral molecule is readily converted to one enantiomer, significantly increasing abundance of one enantiomer. Furthermore, the present inventors also found that an optically active substance including a chiral molecule that is susceptible to racemization, when reacted with a reagent, is converted to a statically chiral molecule or a quasi-statically chiral molecule while maintaining the optical purity thereof, to provide an optically active substance thereof. The present invention has been completed based on these findings and specifically includes configurations below.

(1) A method for producing an optically active substance, the method including an asymmetric induction, wherein an asymmetry inducer is allowed to act on a chiral molecule having a half-life of enantiomeric excess of shorter than 10 hours at 50° C., thereby increasing abundance of one enantiomer of the chiral molecule.

(2) The method for producing an optically active substance according to (1), wherein the asymmetry inducer is allowed to act on the chiral molecule, thereby increasing abundance of one enantiomer without cleavage or reformation of a bond in the chiral molecule.

(3) The method for producing an optically active substance according to (1) or (2), wherein one enantiomer and the other enantiomer of the chiral molecule differ from each other in conformation.

(4) The method for producing an optically active substance according to (2) or (3), wherein the chiral molecule is a planarly asymmetric molecule.

(5) The method for producing an optically active substance according to (2) or (3), wherein the chiral molecule is an axially asymmetric molecule, with the proviso that a substituted biphenyl molecule is excluded.

(6) The method for producing an optically active substance according to (2) or (3), wherein the chiral molecule is a helically asymmetric molecule.

(7) The method for producing an optically active substance according to any one of (1) to (6), wherein the chiral molecule includes a structure represented by any of General Formulas (1) to (3), (4a), (4b), (5), (6), (7), (8), (9a), and (9b) below:

[Chem. 1]

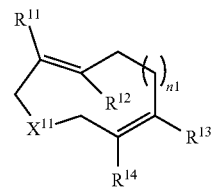

(1)

in General Formula (1), $R^{11}$ to $R^{14}$ each independently represent a hydrogen atom or a substituent; $X^{11}$ represents O, S, or $NR^{15}$, where $R^{15}$ represents a substituent; and n1 represents an integer from 1 to 10;

[Chem. 2]

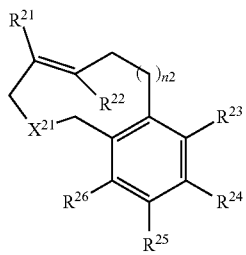

(2)

in General Formula (2), $R^{21}$ and $R^{22}$ each independently represent a hydrogen atom or a substituent; $R^{23}$ to $R^{26}$ each independently represent a hydrogen atom or a substituent; $X^{21}$ represents O, S, or $NR^{27}$, where $R^{27}$ represents a substituent; and n2 represents an integer from 1 to 10;

[Chem. 3]

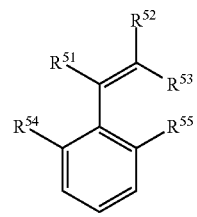

(3)

in General Formula (3), $R^{31}$ and $R^{32}$ each independently represent a substituent, and $R^{33}$ to $R^{37}$ each independently represent a hydrogen atom or a substituent;

[Chem. 4]

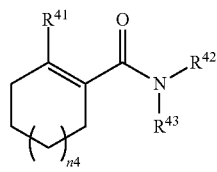

(4a)

in General Formula (4a), $R^{41}$ to $R^{43}$ each independently represent a hydrogen atom of a substituent; n4 represents an integer from 1 to 10; and a cycloalkene backbone in General Formula (4a) may be fused with a benzene ring;

[Chem. 5]

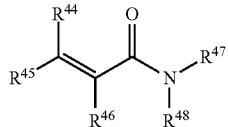

(4b)

in General Formula (4b), $R^{44}$ to $R^{48}$ each independently represent a substituent;

[Chem. 6]

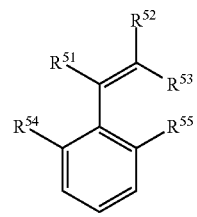

(5)

in General Formula (5), $R^{51}$ to $R^{55}$ each independently represent a substituent, with the proviso that $R^{54}$ and $R^{55}$ are different groups from each other;

[Chem. 7]

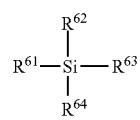

(6)

in General Formula (6), $R^{61}$ to $R^{64}$ are different groups from each other and each independently represent a substituent;

[Chem. 8]

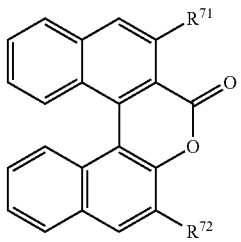

(7)

in General Formula (7), $R^{71}$ and $R^{72}$ each independently represent a hydrogen atom or a substituent;

[Chem. 9]

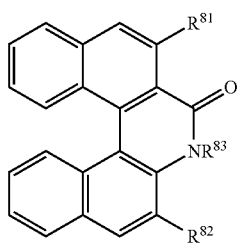

in General Formula (8), $R^{81}$ and $R^{82}$ each independently represent a hydrogen atom or a substituent; and $R^{83}$ represents a substituent;

[Chem. 10]

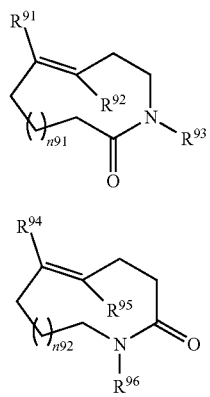

in General Formulas (9a) and (9b), $R^{91}$ to $R^{96}$ each independently represent a substituent; and n91 and n92 each independently represent an integer from 1 to 10.

(8) The method for producing an optically active substance according to any one of (1) to (7), wherein an activation energy required for racemization (hereinafter, a racemization energy) of the chiral molecule is from 20 to 27 kcal/mol.

(9) The method for producing an optically active substance according to any one of (1) to (8), wherein the asymmetry inducer is an optically active substance.

(10) The method for producing an optically active substance according to any one of (1) to (9), wherein the asymmetry inducer is a sugar chain derivative.

(11) The method for producing an optically active substance according to (10), wherein the sugar chain derivative includes a structure in which an aryl group is linked to a sugar chain unit via a linking group, and the linking group contains an ester bond or a urethane bond.

(12) The method for producing an optically active substance according to any one of (1) to (11), wherein the asymmetry inducer is supported by a granular carrier.

(13) The method for producing an optically active substance according to any one of (1) to (12), the method further including an isolation, wherein the one enantiomer is isolated after the asymmetric induction.

(14) The method for producing an optically active substance according to any one of (1) to (13), the method further including an asymmetric stabilization, wherein a reagent is allowed to act on the chiral molecule after the asymmetric induction, thereby converting the one enantiomer to one enantiomer of a second chiral molecule having a longer half-life of enantiomeric excess than that of the chiral molecule.

(15) The method for producing an optically active substance according to (14), wherein the half-life of enantiomeric excess of the second chiral molecule is 10 hours or longer at 50° C.

(16) The method for producing an optically active substance according to (14) or (15), wherein the reagent is an optically active substance.

(17) The method for producing an optically active substance according to (14) or (15), wherein the reagent is an epoxidizing agent.

(18) An optically active substance produced by the production method described in any one of (1) to (17).

(19) A method for producing a chiral molecule, the method including allowing a reagent to act on an optically active substance of a first chiral molecule (a dynamically chiral molecule) having a half-life of enantiomeric excess of shorter than 10 hours at 50° C., of which one enantiomer is present in excess over the other enantiomer, thereby converting the optically active substance of the first chiral molecule to an optically active substance of a second chiral molecule (a statically chiral molecule or a quasi-statically chiral molecule) having a longer half-life of enantiomeric excess (hereinafter, an asymmetric stabilization).

(20) The method for producing a chiral molecule according to (19), the method including allowing an asymmetry inducer to act on a chiral molecule having a half-life of enantiomeric excess of shorter than 10 hours at 50° C. before the asymmetric stabilization, thereby increasing abundance of one enantiomer of the chiral molecule to obtain the first chiral molecule, of which one enantiomer of the chiral molecule is present in excess over the other enantiomer of the chiral molecule.

(21) The method for producing a chiral molecule according to (19) or (20), wherein an enantiomeric excess of the first chiral molecule is 40% ee or greater.

(22) A chiral molecule produced by the production method described in any one of (19) to (21).

(23) The chiral molecule according to (22), having a half-life of enantiomeric excess of 10 hours or longer at 50° C.

Advantageous Effects of Invention

According to the method for producing an optically active substance according to an embodiment of the present invention, one enantiomer of a chiral molecule can be selectively and efficiently obtained. In addition, according to the method of producing a chiral molecule according to an embodiment of the present invention, a stereochemically stable optically active substance in which interconversion is less likely to occur between the enantiomers of the chiral molecule can be obtained. The optically active substance thus obtained is highly useful as a raw material for pharmaceuticals and functional materials.

DESCRIPTION OF EMBODIMENTS

The contents according to an embodiment of the present invention will be described in detail below. The description of the constituent elements provided below may be made based on representative embodiments and specific examples of the present invention, but the present invention is not limited to such embodiments or specific examples. In the present specification, a numerical range expressed by "to" means a range including the numerical values described before and after "to" as the lower limit value and the upper limit value. In addition, the isotopic species of hydrogen atoms present in a molecule of a compound used in an embodiment of the present invention is not particularly limited, and, for example, all the hydrogen atoms in the molecule may be $^1$H, or some or all thereof may be $^2$H (deuterium D).

Method for Producing Optically Active Substance

A method for producing an optically active substance according to an embodiment of the present invention includes allowing an asymmetry inducer to act on a chiral molecule having a half-life of enantiomeric excess of shorter than 10 hours at 50° C., thereby increasing abundance of one enantiomer of the chiral molecule. In an embodiment of the present invention, this process is referred to as an "asymmetric induction". The enantiomer with increased abundance by asymmetric induction is the optically active substance to be produced by the production method according to an embodiment of the present invention. In addition, in an embodiment of the present invention, the term "chiral molecule" does not mean a single molecule but means a collection of molecules.

According to this production method, abundance of one enantiomer of a chiral molecule can be significantly increased without using a chiral reagent and without cleavage or reformation of a bond in the chiral molecule, and the one enantiomer can be selectively and efficiently obtained. Thus, the optical purity can be extremely increased (the enantiomeric excess can be extremely increased). In addition, this production method can be applied to a variety of chiral molecules and is a method that can be widely used for various purposes. This production method is a new method whose concept is completely different from the racemic resolution method and the asymmetric synthesis method known in the art.

The chiral molecule, the asymmetry inducer, and the conditions used in the asymmetric induction according to an embodiment of the present invention will be described in detail below. In the present specification, room temperature means 25° C. as an example.

Asymmetric Induction

In this process, an asymmetry inducer is allowed to act on a chiral molecule having a half-life of enantiomeric excess of shorter than 10 hours, thereby increasing abundance of one enantiomer of the chiral molecule.

Chiral Molecule Having Half-Life of Enantiomeric Excess of Shorter than 10 Hours In an embodiment of the present invention, the "half-life of enantiomeric excess" of a chiral molecule used in the asymmetric induction refers to the time until the enantiomeric excess of the chiral molecule becomes ½ of the initial enantiomeric excess at a certain temperature.

In addition, the enantiomeric excess is a value determined by Equation (I) below.

[Equation 1]

$$\text{Enantiomeric excess } (\% \ ee) = \left(\frac{A_1 - A_2}{A_1 + A_2}\right) \times 100 \quad (I)$$

In Equation (I), $A_1$ and $A_2$ represent mole fractions of one and the other enantiomers contained in the chiral molecule of interest, where $A_1$ is a mole fraction of an enantiomer having a larger mole fraction, and $A_2$ is a mole fraction of an enantiomer having a smaller mole fraction.

The mole fractions of one and the other enantiomers can be determined by methods, such as HPLC-GC analysis using a chiral stationary phase, an optical rotation measurement, and NMR analysis using a chiral shift reagent.

A chiral molecule of which one or the other enantiomer is present in excess exhibits optical activity, and thus such a chiral molecule may be referred in the present specification to as an "optically active substance".

Chiral molecules are susceptible to interconversion between enantiomers, and the more susceptible to racemization, the shorter the half-life of enantiomeric excess. Thus, a chiral molecule having a half-life of enantiomeric excess of shorter than 10 hours at 50° C. is readily converted to one enantiomer from the other enantiomer by allowing an appropriate asymmetry inducer to act thereon under mild temperature conditions (from 0 to 50° C.), and abundance of the one enantiomer can be increased. The half-life of enantiomeric excess of the chiral molecule (dynamically chiral molecule) used in the method for producing an optically active substance according to an embodiment of the present invention can be, for example, shorter than 5 hours, shorter than 3 hours, or shorter than 1 hour. The lower limit of the half-life of enantiomeric excess of the chiral molecule is not particularly limited, but in terms of stereochemical stability of the chiral molecule and resulting ease of handling, it can be, for example, 10 minutes or longer, 1 hour or longer, and 10 hours or longer at a temperature, for example, lower than 0° C.

As the chiral molecule used in the asymmetric induction, for example, a chiral molecule whose enantiomers differ from each other in conformation, i.e., a chiral molecule exhibiting chirality due to a difference in conformation can be used. Such a chiral molecule changes to one enantiomer from the other enantiomer by conformational conversion, such as rotation of a bond in the molecule or a change in the bond angle, with a relatively low energy barrier (for example, 20 kcal/mol or several greater than 20 kcal/mol). Thus, the other enantiomer is readily changed to one enantiomer by allowing an asymmetry inducer to act on a chiral molecule under mild conditions at approximately room temperature, and abundance of the one enantiomer can be significantly increased. Examples of chiral molecules whose enantiomers differ from each other in conformation may include planarly asymmetric molecules, axially asymmetric molecules (for example, axially asymmetric molecules other than substituted biphenyl molecules can be selected), helically asymmetric molecules, and centrally asymmetric molecules. Examples of the planarly asymmetric molecule may include a cyclic diene and an ortho-cyclophene. Examples of the axially asymmetric molecule may include an anilide, an unsaturated amide, and a substituted styrene, and, for example, an axially asymmetric molecule other than substituted biphenyl molecules can be also selected. Examples of the helically asymmetric molecule include a lactone and a lactam. Examples of the centrally asymmetric molecule include a silane. Specifically, for example, compounds represented by General Formulas (1) to (3), (4a), (4b), (5), (6), (7), (8), (9a), and (9b) below can be employed. In any of the compounds represented by these general formulas, enantiomers thereof readily interconvert to each other under mild temperature conditions (from 0 to 50° C.), and thus the temperature when the asymmetry inducer is allowed to act can be set to mild temperature conditions (from 0 to 50° C.).

First, as the cyclic diene used as the chiral molecule, a compound represented by General Formula (1) below can be used.

[Chem. 11]

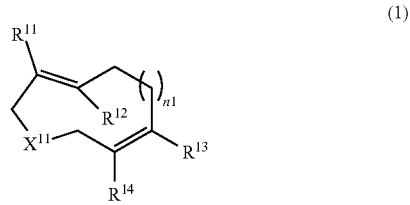

(1)

In General Formula (1), $R^{11}$ to $R^{14}$ each independently represent a hydrogen atom or a substituent; substituents represented by $R^{11}$ to $R^{14}$ may be the same or different from each other; $X^{11}$ represents O, S, or $NR^{15}$, where $R^{15}$ represents a substituent; and n1 represents an integer from 1 to 10.

The substituents are not particularly limited, but as the substituent represented by $R^{12}$, for example, a substituted or unsubstituted alkyl group or a halogen atom can be used, and when a substituted alkyl group is used, an alkyl group substituted with a halogen atom, or an alkyl group substituted with a substituted or unsubstituted acyloxy group can be used. As the substituent represented by $R^{15}$, for example, a protecting group, such as a tosyl group, can be used.

As the ortho-cyclophene used as the chiral molecule, a compound represented by General Formula (2) below can be used.

[Chem. 12]

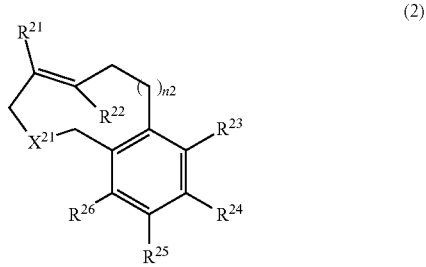

(2)

In General Formula (2), $R^{21}$ and $R^{22}$ each independently represent a hydrogen atom or a substituent. When both $R^{21}$ and $R^{22}$ represent substituents, the substituents may be the same or different from each other. One aspect may include the case where either one of $R^{21}$ or $R^{22}$ is a hydrogen atom and the other is a substituent. $R^{23}$ to $R^{26}$ each independently represent a hydrogen atom or a substituent. The number of the substituent in $R^{23}$ to $R^{26}$ is not particularly limited, and all of $R^{23}$ to $R^{26}$ may be unsubstituted (hydrogen atoms). When two or more of $R^{21}$ to $R^{26}$ are substituents, a plurality of the substituents may be the same or different from each other. $X^{21}$ represents O, S, or $NR^{27}$, where $R^{27}$ represents a substituent, and n2 represents an integer from 1 to 10.

The type of the substituent is not particularly limited, but as the substituent represented by $R^{22}$, for example, a substituted or unsubstituted alkyl group or a halogen atom can be used, and when a substituted alkyl group is used, an alkyl group substituted with a halogen atom or an alkyl group substituted with an acyloxy group can be used. As the substituent represented by $R^{27}$, for example, a protecting group, such as a tosyl group, can be used.

Conformations of R and S enantiomers of an example of the compounds represented by General Formulas (1) and (2) are schematically illustrated below, where X and Y represent substituents.

[Chem. 13]

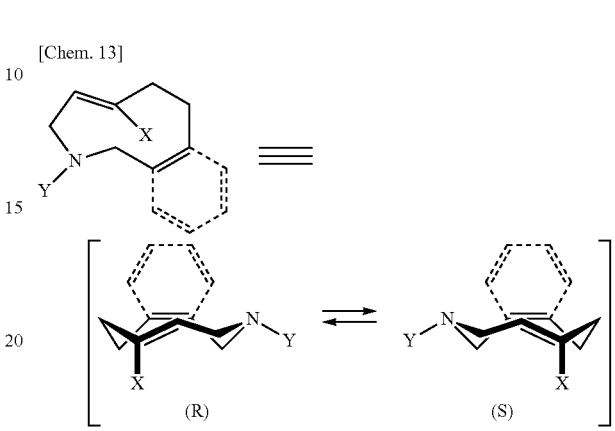

As the anilide used as the chiral molecule, a compound represented by General Formula (3) below can be used.

[Chem. 14]

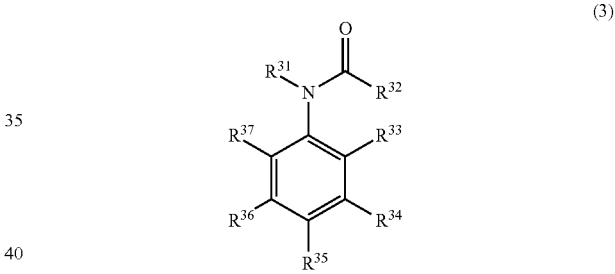

(3)

In General Formula (3), $R^{31}$ and $R^{32}$ each independently represent a substituent. The substituents represented by $R^{31}$ and $R^{32}$ may be the same or different from each other. $R^{33}$ to $R^{37}$ each independently represent a hydrogen atom or a substituent. The number of the substituent in $R^{33}$ to $R^{37}$ is not particularly limited, and all of $R^{33}$ to $R^{37}$ may be unsubstituted (hydrogen atoms). When two or more of $R^{33}$ to $R^{37}$ are substituents, a plurality of the substituents may be the same or different from each other.

The substituents are not particularly limited, but as the substituent represented by $R^{31}$, for example, a substituted or unsubstituted alkyl group can be used, and when a substituted alkyl group is used, an alkyl group substituted with a substituted or unsubstituted aryl group, or an alkyl group substituted with a substituted or unsubstituted heteroaryl group can be used. As the substituent represented by $R^{32}$, for example, a substituted or unsubstituted alkyl group or a substituted or unsubstituted alkenyl group can be used, and when a substituted alkyl group or a substituted alkenyl group is used, an alkyl group substituted with a substituted or unsubstituted aryl group, or an alkenyl group substituted with a substituted or unsubstituted aryl group can be used. As the substituents represented by $R^{33}$ and $R^{37}$, for example, a substituted or unsubstituted alkyl group or a halogen atom can be used.

Conformations of R and S enantiomers of an example of the compound represented by General Formula (3) are schematically illustrated below, where R, R', X, and Y represent substituents.

[Chem. 15]

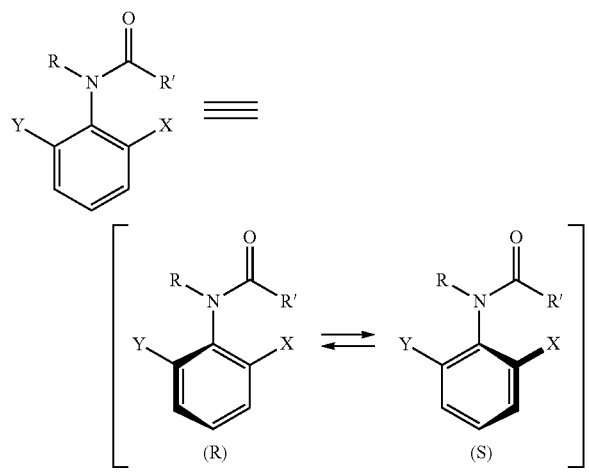

As the unsaturated amide used as the chiral molecule, a compound represented by General Formula (4a) or (4b) below can be used.

[Chem. 16]

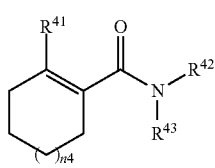

(4a)

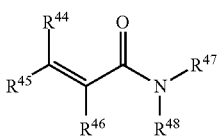

(4b)

In General Formulas (4a) and (4b), $R^{41}$ to $R^{43}$, and $R^{44}$ to $R^{48}$ each independently represent a substituent; substituents represented by $R^{41}$ to $R^{43}$ may be the same or different from each other; substituents represented by $R^{44}$ to $R^{48}$ may be the same or different from each other; n4 represents an integer from 1 to 10; and a cycloalkene backbone in General Formula (4a) may be fused with a benzene ring.

The substituents are not particularly limited, but as the substituent represented by $R^{41}$, for example, a substituted or unsubstituted aryloyloxy group or a substituted or unsubstituted silyloxy group can be used, and when a substituted aryloyloxy group is used, an aryloyloxy group substituted with a substituted or unsubstituted alkoxy group can be used, and when a substituted silyloxy group is used, a silyloxy group in which three hydrogen atoms are substituted with at least one of a substituted or unsubstituted alkyl group or a substituted or unsubstituted aryl group can be used. As the substituents represented by $R^{42}$, $R^{43}$, $R^{47}$, and $R^{48}$, for example, a substituted or unsubstituted alkyl group can be used.

Conformations of R and S enantiomers of an example of the compound represented by General Formula (4a) are schematically illustrated below, where R and X represent substituents.

[Chem. 17]

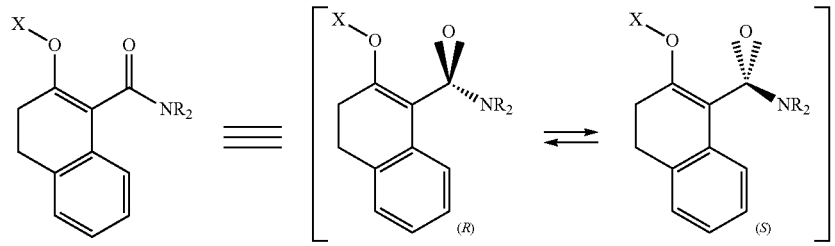

As the substituted stylene used as the chiral molecule, a compound represented by General Formula (5) can be used.

[Chem. 18]

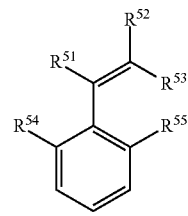

(5)

In General Formula (5), $R^{51}$ to $R^{55}$ each independently represent a substituent, with the proviso that $R^{54}$ and $R^{55}$ are different groups from each other.

The substituents are not particularly limited, but as the substituents represented by $R^{51}$ to $R^{53}$, for example, a substituted or unsubstituted alkyl group can be used. As the substituents represented by $R^{54}$ and $R^{55}$, for example, a substituted or unsubstituted alkyl group, a substituted or unsubstituted alkoxy group, or a halogen atom can be used.

As the silane used as the chiral molecule, a compound represented by General Formula (6) can be used.

[Chem. 19]

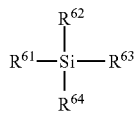
(6)

In General Formula (6), $R^{61}$ to $R^{64}$ are different groups from each other and each independently represent a substituent.

The substituents are not particularly limited, but as the substituents represented by $R^{61}$ and $R^{62}$, for example, a substituted or unsubstituted alkyl group can be used. As the substituents represented by $R^{63}$ and $R^{64}$, a substituted or unsubstituted alkyl group, a substituted or unsubstituted alkoxy group, or a halogen atom can be used.

As the lactone used as the chiral molecule, a compound represented by General Formula (7) can be used.

[Chem. 20]

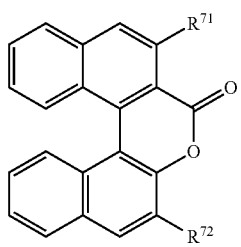
(7)

In General Formula (7), $R^{71}$ and $R^{72}$ each independently represent a hydrogen atom or a substituent. The number of the substituent in $R^{71}$ and $R^{72}$ is not particularly limited, and both $R^{71}$ and $R^{72}$ may be unsubstituted (hydrogen atoms). When both $R^{71}$ and $R^{72}$ are substituents, the two substituents may be the same or different from each other.

The substituents represented by $R^{71}$ and $R^{72}$ are not particularly limited, but for example, a substituted or unsubstituted alkoxy group can be used, and when a substituted alkoxy group is used, an alkoxy group substituted with a substituted or unsubstituted aryl group, or an alkoxy group substituted with a substituted or unsubstituted alkoxy group can be used. Furthermore, examples of the substituent of the substituted alkoxy group in the alkoxy group substituted with the substituted alkoxy group include a substituted or unsubstituted alkoxy group and a silyl group in which three hydrogen atoms substituted with an alkyl group are substituted.

Conformations of R and S enantiomers of an example of the compound represented by General Formula (7) are schematically illustrated below, where X and Y represent substituents.

[Chem. 21]

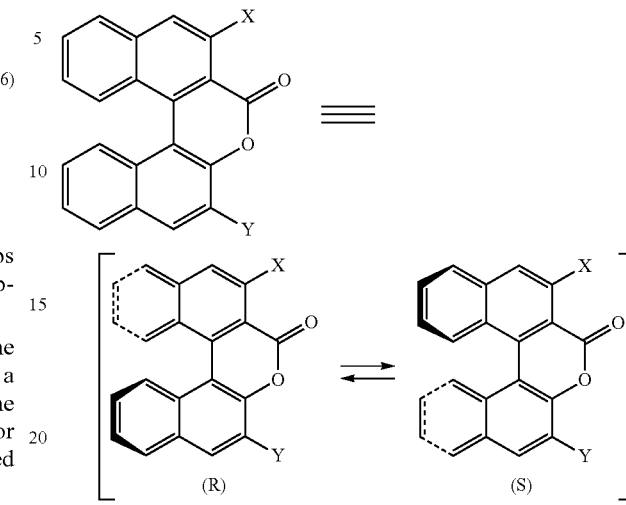

As the lactam used as the chiral molecule, a compound represented by General Formula (8) can be used.

[Chem. 22]

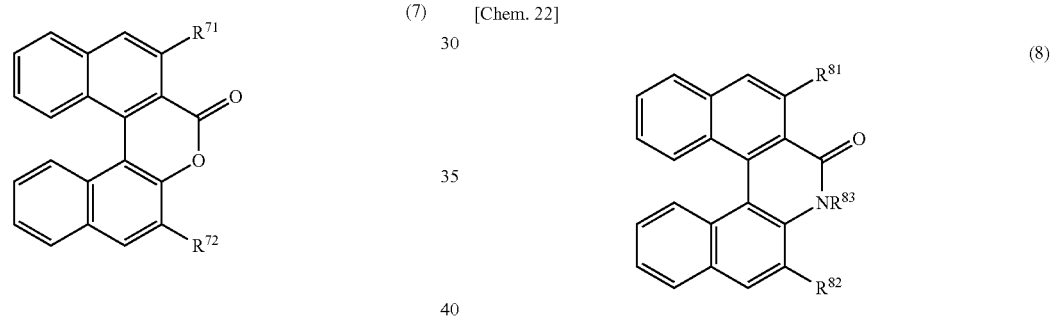
(8)

In General Formula (8), $R^{81}$ and $R^{82}$ each independently represent a hydrogen atom or a substituent. The number of the substituent in $R^{81}$ and $R^{82}$ is not particularly limited, and both $R^{81}$ and $R^{82}$ may be unsubstituted (hydrogen atoms). When both $R^{81}$ and $R^{82}$ are substituents, the two substituents may be the same or different from each other. $R^{83}$ represents a substituent.

The substituents are not particularly limited, but as the substituents represented by $R^{81}$ and $R^{82}$, for example, a substituted or unsubstituted alkoxy group can be used, and when a substituted alkoxy group is used, an alkoxy group substituted with a substituted or unsubstituted aryl group, or an alkoxy group substituted with a substituted or unsubstituted alkoxy group can be used. Furthermore, examples of the substituent of the substituted alkoxy group in the alkoxy group substituted with the substituted alkoxy group include a substituted or unsubstituted alkoxy group and a silyl group in which three hydrogen atoms substituted with an alkyl group are substituted.

As the lactams that can be used as the chiral molecule, a compound represented by General Formula (9a) or (9b) can also be used.

[Chem. 23]

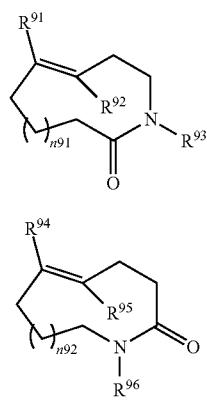

In General Formulas (9a) and (9b), $R^{91}$ to $R^{96}$ each independently represent a substituent, and n91 and n92 each independently represent an integer from 1 to 10.

The substituents are not particularly limited, but as the substituents represented by $R^{91}$, $R^{92}$, $R^{94}$, and $R^{95}$, for example, a substituted or unsubstituted alkyl group can be used. As the substituents represented by $R^{93}$ and $R^{96}$, for example, a substituted or unsubstituted alkyl group, a substituted or unsubstituted acyl group, a substituted or unsubstituted alkoxycarbonyl group, or a sulfonyl group can be used. As the acyl group, for example, an acetyl group or a benzyl group can be used. As the alkoxycarbonyl group, for example, a tert-butoxycarbonyl group (Boc group) can be used. As the sulfonyl group, a p-toluenesulfonyl group (tosyl group, Ts group), a 2-nitrobenzenesulfonyl group (nosyl group, Ns group), or a methanesulfonyl group (mesyl group, Ms group) can be used.

Examples of the substituents that can be $R^{11}$ to $R^{15}$ of General Formula (1), $R^{21}$ to $R^{27}$ of General Formula (2), $R^{31}$ to $R^{37}$ of General Formula (3), $R^{41}$ to $R^{43}$ of General Formula (4a), $R^{44}$ to $R^{48}$ of General Formula (4b), $R^{51}$ to $R^{55}$ of General Formula (5), $R^{61}$ to $R^{64}$ of General Formula (6b), $R^{71}$ and $R^{72}$ of General Formula (7), $R^{81}$ to $R^{83}$ of General Formula (8), $R^{91}$ to $R^{93}$ of General Formula (9a), $R^{94}$ to $R^{96}$ of General Formula (9b), and the substituents that can substitute the substituents exemplified by each general formula include a hydroxy group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, a diarylamino group having from 12 to 40 carbon atoms, a substituted or unsubstituted carbazolyl group having from 12 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. Of these specific examples, the substituent that can be further substituted with a substituent may be substituted with the substituent of these specific examples.

The "alkyl group" or the alkyl group in the substituent containing an alkyl group in a portion thereof in the present specification may be any of linear, branched, or cyclic alkyl group having a certain number of carbon atoms that can be selected, for example, from 1 to 10, from 1 to 6, or from 1 to 3. Examples thereof include a methyl group, an ethyl group, and a propyl group. In addition, specific examples of the "halogen atom" in the present specification include a fluorine atom, a chlorine atom, a bromine atom, and an iodine atom.

The chiral molecule used in the asymmetric induction can have a racemization energy of, for example, 27 kcal/mol or less, 25 kcal/mol or less, 24 kcal/mol, or 23 kcal/mol or less. In addition, the chiral molecule used in the asymmetric induction can have a racemization energy of, for example, 20 kcal/mol or greater, 21 kcal/mol or greater, or 22 kcal/mol or greater. The range of the racemization energy may include, for example, a range from 21 to 23 kcal/mol. A chiral molecule having an appropriate range of the racemization energy, while having the appropriate stereochemical stability to the extent that it is slowly racemized at room temperature, changes relatively easily to one enantiomer from the other enantiomer if an appropriate asymmetry inducer is allowed to act thereon at room temperature. Thus, by subjecting a chiral molecule having such racemization energy to the production method according to an embodiment of the present invention, one enantiomer can be selectively and efficiently obtained, and the chiral molecule can be well handled.

The racemization energy of the chiral molecule can be determined by kinetic analysis experiment or by density functional theory calculation (DFT calculation) of a racemic transition state.

Specific examples of the chiral molecules having a half-life of enantiomeric excess of shorter than 10 hours at 25° C. that can be used in an embodiment of the present invention will be shown below. However, the chiral molecules having a half-life of enantiomeric excess of shorter than 10 hours at 25° C. that can be used in an embodiment of the present invention should not be construed as being limited by these specific examples. In the formulas below, Ts represents a tosyl group (p-toluenesulfonyl group), Ac represents an acetyl group, iPr represents an isopropyl group, Ph represents a phenyl group, TBDPS represents a t-butyldiphenylsilyl group, Bn represents a benzyl group, MEM represents a 2-methoxyethoxymethyl group, and SEM represents a 2-(trimethylsilyl)ethoxymethyl group.

[Chem. 24]

Compound 1

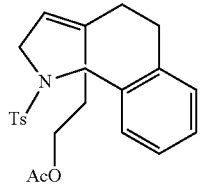

Compound 2

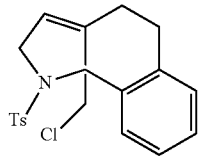

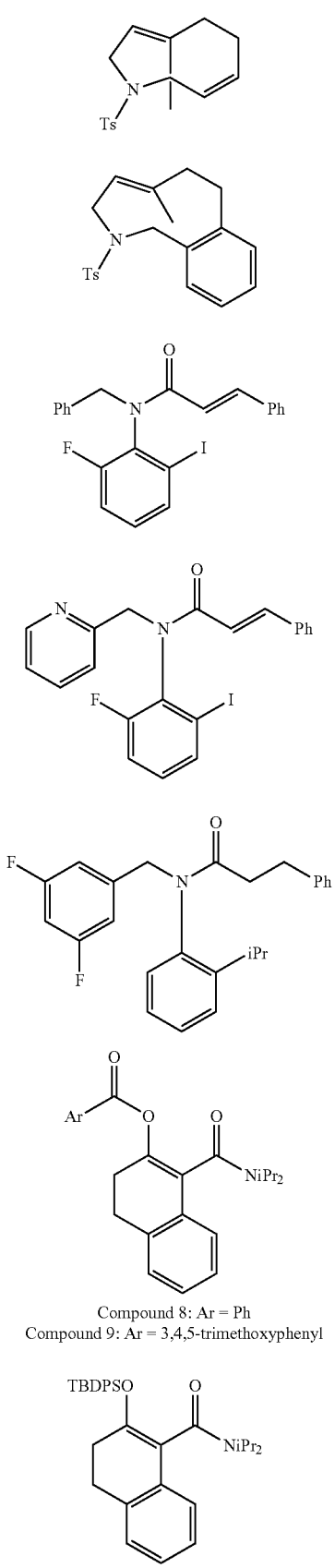

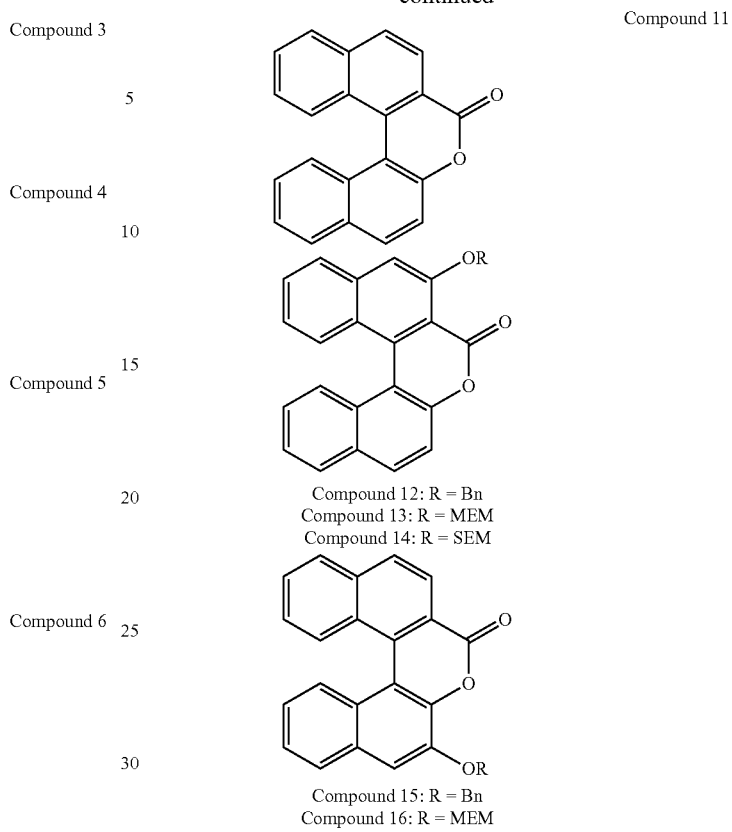

Asymmetry Inducer

In an embodiment of the present invention, "asymmetry inducer" refers to a substance that, when allowed to act on a chiral molecule, acts to increase the abundance of one enantiomer of the chiral molecule. The asymmetry inducer, when allowed to act on the chiral molecule, needs to be a substance that increases the abundance of one enantiomer without the cleavage or reformation of a bond in the chiral molecule. The asymmetry inducer may be recovered and reused. In addition, the asymmetry inducer may also be a substance that has a function of preferentially interacting with the other enantiomer to convert the conformation of the other enantiomer to the conformation of one enantiomer.

Examples of such asymmetry inducers include sugar chain derivatives (sugar chain derivative polymers), such as cellulose derivatives and amylose derivatives; naturally derived chiral polymers and derivatives thereof, such as polypeptides, DNA, and antibodies; amino acid derivatives; and chiral template polymers (artificial chiral polymers).

The asymmetry inducer may be supported by a granular carrier, such as silica gel. Thereby, the asymmetry inducer after allowed to act on the chiral molecule in the solvent can be easily separated from the chiral molecule by a simple operation, such as filtration, and be reused.

Method and Conditions for Allowing Asymmetry Inducer to Act on Chiral Molecule

As described above, in the method for producing an optically active substance according to an embodiment of the present invention, an asymmetry inducer is allowed to act on a chiral molecule having a half-life of enantiomeric excess of shorter than 10 hours at 50° C.

The operation of allowing the asymmetry inducer to act on the chiral molecule can be performed by allowing the chiral molecule and the asymmetry inducer to coexist in a solvent, stirring the solvent, and then allowing the solvent to stand. The stirring the solvent allows the asymmetry inducer to be in sufficient contact with the chiral molecule, and then by allowing it to stand, the effect of the asymmetry inducer can be exhibited and the equilibrium between the enantiomers can be sufficiently biased. Here, after the solvent in which the chiral molecule and the asymmetry inducer are allowed to coexist is stirred, the solvent may be distilled off, and another solvent may be added instead, and the chiral molecule and the asymmetry inducer may be allowed to stand in the solvent.

The solvent is not particularly limited and may be any solvent that does not adversely affect the chiral molecule or the asymmetry inducer and does not impair the effect of the asymmetry inducer. The solvent may be miscible with the chiral molecule, and the asymmetry inducer or the carrier by which the asymmetry inducer is supported may be present in the solvent in a solid state. Since the chiral molecule is dissolved in the solvent, and the asymmetry inducer or the carrier by which the asymmetry inducer is supported is present in a solid state, the asymmetry inducer after allowed to act on the chiral molecule can be easily separated from the chiral molecule by a simple operation, such as filtration. In addition, the solvent may have a higher vapor pressure (lower boiling point) than that of the chiral molecule. Thereby, the solvent and the chiral molecule can be easily separated by a simple operation, such as distillation.

The amount of the solvent when allowing the chiral molecule and the asymmetry inducer to stand can be from 1 to 20 times the total amount of the chiral molecule and the asymmetry inducer.

The amount of the asymmetry inducer in the solvent can be, for example, 50 times or greater, 100 times or greater, 200 times or greater, and 1000 times or less, 500 times or less, 300 times or less relative to the weight of the chiral molecule.

The temperature of the solvent when the chiral molecule and the asymmetry inducer are allowed to stand can be, for example, from 0 to 50° C. The method for producing an optically active substance according to an embodiment of the present invention allows treatment under mild temperature conditions (from 0 to 50° C.) as described above, and thus an apparatus, an instrument, or an operation for high temperature heating is unnecessary, and a production costs of the optically active substance can be kept low.

An amount of time that the chiral molecule and the asymmetry inducer are allowed to stand can be 72 hours or shorter in terms of operational efficiency.

Additional Process

In the method for producing an optically active substance according to an embodiment of the present invention, the following can be performed after the asymmetric induction: isolating the optically active substance (isolation); and allowing a reagent to act on the chiral molecule, thereby converting the optically active substance to an optically active substance of a second chiral molecule having a longer half-life of enantiomeric excess than that of the chiral molecule (asymmetric stabilization). Each process will be described below.

Isolation

The optically active substance obtained in the above asymmetric induction coexists with the asymmetry inducer in a solvent. In the isolation, the optically active substance is isolated from these materials.

In a case where the asymmetry inducer is solid in the solvent or is supported by a solid carrier, the optically active substance and the asymmetry inducer can be separated by filtering a mixture of the optically active substance, the asymmetry inducer, and the solvent. Thereby, the asymmetry inducer remains on the filter material while the optically active substance is dissolved in the filtrate, and thus both are separated. In addition, the optically active substance and the solvent can be separated by distilling off the solvent. Either of filtration or distillation may be performed first, but if distillation is performed first, a solvent is newly added to the concentrate after the distillation before performing filtration.

In addition, the separated asymmetry inducer can be reused as an asymmetry inducer in the asymmetric induction.

Also, if the enantiomeric excess of one enantiomer in the filtrate is not 100% ee, i.e., the other enantiomer is contained in the filtrate, the operation may be performed to separate the other enantiomer from one enantiomer. One enantiomer and the other enantiomer can be separated by applying a well-known optical resolution method. One enantiomer and the other enantiomer may be separated after the asymmetric stabilization.

Asymmetric Stabilization

In the above asymmetric induction, one enantiomer with an increased abundance may change to the other enantiomer over time. In the asymmetric stabilization, a reagent is allowed to act on the chiral molecule that has become an optically active substance in the asymmetric induction to convert the optically active substance to an optically active substance of a second chiral molecule that has a longer half-life of enantiomeric excess than that of the chiral molecule. Thereby, an optically active substance having high optical purity and having stable optical activity can be obtained. The asymmetric stabilization may be performed after the asymmetric induction or may be performed after the above isolation.

Reagent

The "reagent" in the asymmetric stabilization is a substance that has a function of reacting with the optically active substance obtained in the above asymmetric induction to convert it to an optically active substance of a second racemic molecule having a longer half-life of enantiomeric excess than the racemic molecule used in the asymmetric induction. As the reagent, any substances having such a function can be used without any particular limit. The subject actually treated with the reagent may be a chiral molecule consisting of only one enantiomer isolated, or a chiral molecule including one enantiomer and the other enantiomer, in which one enantiomer is present in excess over the other enantiomer. When a mixture including one enantiomer and the other enantiomer is treated with an asymmetry inducer, the other enantiomer may also undergo the action of the reagent.

Examples of the reagent include an epoxidizing agent, an alkyllithium reagent, an alkylmagnesium reagent, and a metal alkoxide reagent.

The method and conditions for allowing the reagent to act on the optically active substance are not particularly limited. For example, when an epoxidizing agent is used as the reagent, the asymmetric stabilization can be performed by the method and conditions for the asymmetric stabilization described in the section of Examples.

Second Chiral Molecule

The "half-life of enantiomeric excess" of the second chiral molecule used in the asymmetric stabilization refers to the time until the enantiomeric excess of one enantiomer of the second chiral molecule becomes ½ of the initial enantiomeric excess at a certain temperature, where the "one enantiomer" is the target enantiomer (one enantiomer) to be obtained in the asymmetric stabilization.

In the asymmetric stabilization, the half-life of enantiomeric excess of the second chiral molecule refers to the time until the initial enantiomeric excess of one enantiomer becomes ½ of the initial enantiomeric excess at a certain temperature, where the "one enantiomer" is the enantiomer (one enantiomer) with an abundance increased in the asymmetric induction.

The half-life of enantiomeric excess of the second chiral molecule can be, for example, 10 hours or longer, 100 hours or longer, or 1,000 hours or longer at 50° C.

The compound that can be employed as the second chiral molecule, i.e., the chiral molecule having a relatively long half-life of enantiomeric excess, may include planarly asymmetric molecules, 5-membered ring compounds, cyclohexane derivatives, tetrahydronaphthalene derivatives, epoxides, ortho-cyclophanes, indolones, and binaphthyl compounds.

As the planarly asymmetric molecule as the second chiral molecule, a compound represented by General Formula (10) or (11) below can be used.

[Chem. 25]

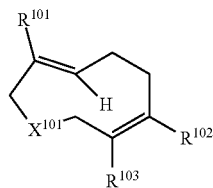

(10)

In General Formula (10), $R^{101}$ to $R^{103}$ each independently represent a hydrogen atom or a substituent. The number of the substituent in $R^{101}$ to $R^{103}$ is not particularly limited, and all of $R^{101}$ to $R^{103}$ may be unsubstituted (hydrogen atoms). When two or more of $R^{101}$ to $R^{103}$ are substituents, a plurality of the substituents may be the same or different from each other. $X^{101}$ represents O, S, or $NR^{104}$, where $R^{104}$ represents a substituent.

The substituent is not particularly limited, but $R^{104}$ can be a protecting group, such as a tosyl group.

[Chem. 26]

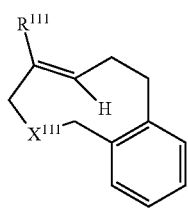

(11)

In General Formula (11), $R^{111}$ represents a hydrogen atom or a substituent. $X^{111}$ represents O, S, or $NR^{112}$, where $R^{112}$ represents a substituent. $R^{112}$ can be a protecting group, such as a tosyl group.

The 5-membered ring compound as the second chiral molecule can be a compound represented by General Formula (12) below.

[Chem. 27]

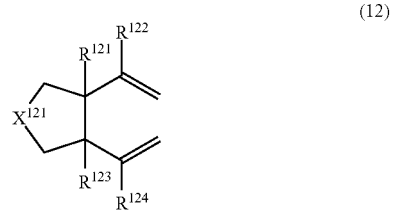

(12)

In General Formula (12), $R^{121}$ to $R^{124}$ each independently represent a hydrogen atom or a substituent. The number of the substituent in $R^{121}$ to $R^{124}$ is not particularly limited, and all of $R^{121}$ to $R^{124}$ may be unsubstituted (hydrogen atoms). When two or more of $R^{121}$ to $R^{124}$ are substituents, a plurality of the substituents may be the same or different from each other. $X^{121}$ represents O, S, or $NR^{125}$, and $R^{125}$ represents a substituent.

The cyclohexane derivative as the second chiral molecule can be a compound represented by General Formula (13) below.

[Chem. 28]

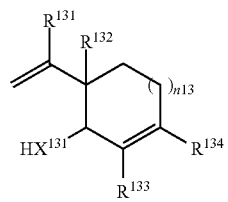

(13)

In General Formula (13), $R^{131}$ to $R^{134}$ each independently represent a hydrogen atom or a substituent. The number of the substituent in $R^{131}$ to $R^{134}$ is not particularly limited, and all of $R^{131}$ to $R^{134}$ may be unsubstituted (hydrogen atoms). When two or more of $R^{131}$ to $R^{134}$ are substituents, a plurality of the substituents may be the same or different from each other. $X^{131}$ represents O, S, or $NR^{135}$, where $R^{135}$ represents a substituent. n13 represents an integer from 1 to 10.

The substituent is not particularly limited, but the substituent represented by $R^{132}$ can be an alkyl group substituted with a hydroxyl group, and the substituent represented by $R^{135}$ can be a protecting group, such as a tosyl group.

The tetrahydronaphthalene derivative as the second chiral molecule can be a compound represented by General Formula (14) below.

[Chem. 29]

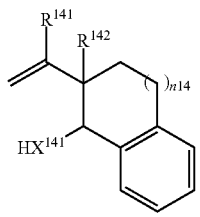

(14)

In General Formula (14), $R^{141}$ and $R^{142}$ each independently represent a hydrogen atom or a substituent. The number of the substituent in $R^{141}$ and $R^{142}$ is not particularly limited, and both $R^{141}$ and $R^{142}$ may be unsubstituted (hydrogen atoms). When both $R^{141}$ and $R^{142}$ are substituents, the two substituents may be the same or different from each other. X represents O, S, or $NR^{143}$, where $R^{143}$ represents a substituent. n14 represents an integer from 1 to 10.

The substituent is not particularly limited, but the substituent represented by $R^{142}$ can be, for example, an alkyl group substituted with a hydroxyl group, and the substituent represented by $R^{143}$ can be a protecting group, such as a tosyl group.

The epoxide as the second chiral molecule can be an epoxide represented by General Formulas (15), (16), (17), or (18). Specific examples of the second chiral molecule may include those represented by the following general formulas.

The ortho-cyclophane as the second chiral molecule can be compounds represented by General Formulas (15) to (19) below.

[Chem. 30]

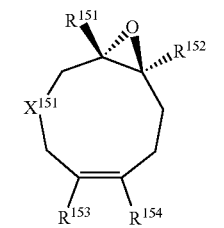

(15)

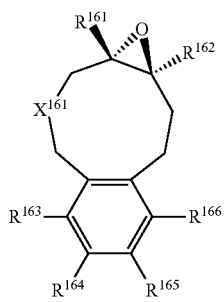

(16)

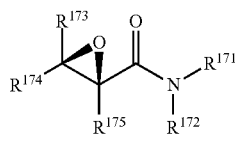

(17)

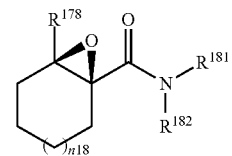

(18)

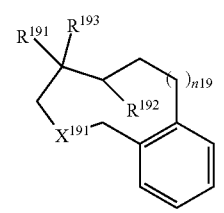

(19)

In General Formulas (15) to (19), $R^{151}$ to $R^{154}$, $R^{161}$ to $R^{165}$, $R^{171}$ to $R^{175}$, $R^{181}$ to $R^{183}$, and $R^{191}$ to $R^{193}$ each independently represent a hydrogen atom or a substituent. The number of the substituent in $R^{151}$ to $R^{154}$, $R^{161}$ to $R^{165}$, $R^{171}$ to $R^{175}$, $R^{181}$ to $R^{183}$, and $R^{191}$ to $R^{193}$ is not particularly limited, and all may be unsubstituted (hydrogen atoms). When two or more are substituents, a plurality of the substituents may be the same or different from each other. $X^{151}$, $X^{161}$, and $X^{191}$ each independently represent O, S, or $NR^{194}$, where $R^{194}$ represents a substituent. n18 and n19 each independently represent an integer from 1 to 10.

The indolone as the second chiral molecule can be a compound represented by General Formula (20) below.

[Chem. 31]

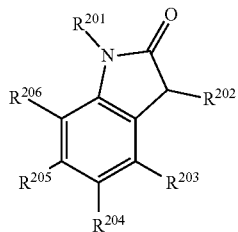

(20)

In General Formula (20), $R^{201}$ represents a substituent, and $R^{202}$ to $R^{206}$ each independently represent a hydrogen atom or a substituent. The number of the substituent in $R^{202}$ to $R^{206}$ is not particularly limited, and all of $R^{202}$ to $R^{206}$ may be unsubstituted (hydrogen atoms). When two or more of $R^{201}$ to $R^{206}$ are substituents, a plurality of the substituents may be the same or different from each other.

The binaphthyl compound as the second chiral molecule can be a compound represented by General Formula (21) or (22).

[Chem. 32]

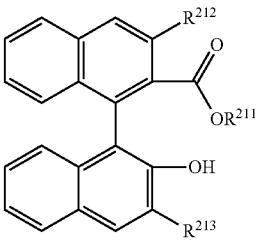

(21)

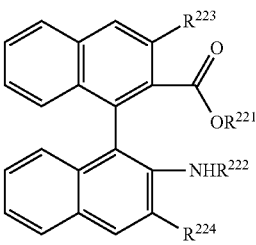

(22)

In General Formulas (21) and (22), $R^{211}$, $R^{221}$, and $R^{222}$ each independently represent a substituent. $R^{212}$, $R^{213}$, $R^{223}$, and $R^{224}$ each independently represent a hydrogen atom or a substituent. For example, at least one of $R^{212}$ or $R^{213}$ and at least one of $R^{223}$ or $R^{224}$ can be a substituent. The substituents represented by $R^{211}$ to $R^{213}$ and $R^{221}$ to $R^{224}$ may be the same or different.

The substituents are not particularly limited, but the substituent represented by $R^{211}$ and $R^{221}$ can be, for example, a substituted or unsubstituted alkyl group.

For the scope and specific examples of the substituents that can be $R^{101}$ to $R^{104}$ of General Formula (10), $R^{111}$ and $R^{112}$ of General Formula (11), $R^{121}$ to $R^{125}$ of General Formula (12), $R^{131}$ to $R^{135}$ of General Formula (13), $R^{141}$ to $R^{143}$ of General Formula (14), $R^{191}$ to $R^{194}$ of General Formula (19), $R^{201}$ to $R^{206}$ of General Formula (20), $R^{211}$ of General Formula (21), and $R^{221}$ and $R^{222}$ of General Formula (22), reference can be made to the scope and specific examples of the substituents that can be $R^{11}$ to $R^{15}$ of General Formula (1) and the like.

Specific examples of the second chiral molecule that can be used in an embodiment of the present invention will be shown below. However, the second chiral molecule that can be used in an embodiment of the present invention should not be construed as being limited by these specific examples. In the following formulas, Ac represents an acetyl group, Ts represents a tosyl group (p-toluenesulfonyl group), TBDPS represents a t-butyldiphenylsilyl group, iPr represents an isopropyl group, Et represents an ethyl group, and SEM represents a 2-(trimethylsilyl)ethoxymethyl group.

[Chem. 33]

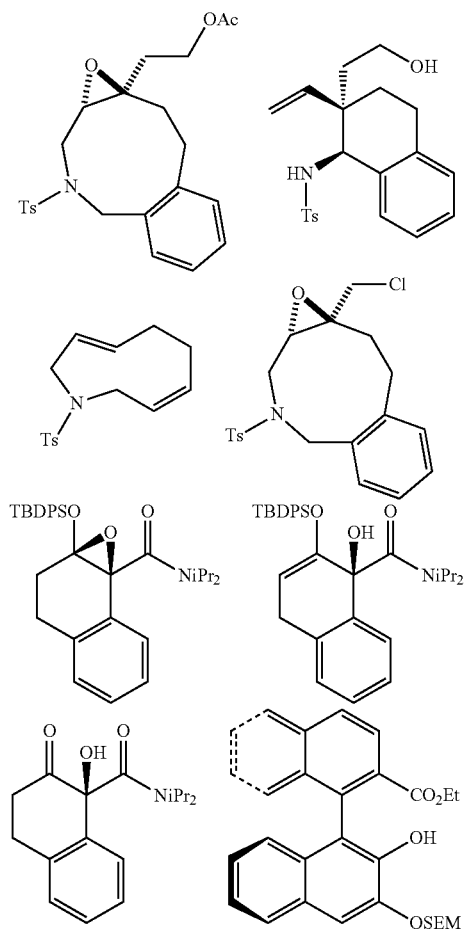

Optically Active Substance

Next, the optically active substance according to an embodiment of the present invention will be described.

The optically active substance according to an embodiment of the present invention is produced by the method for producing an optically active substance according to an embodiment of the present invention.

For the description, scope, and specific examples of the method for producing an optically active substance according to an embodiment of the present invention, reference can be made to the contents described in the above section of method for producing optically active substance.

The optically active substance according to an embodiment of the present invention may be an optically active substance obtained in the asymmetric induction in the method for producing an optically active substance according to an embodiment of the present invention, an optically active substance isolated by performing the isolation after the asymmetric induction, an optically active substance of the second chiral molecule obtained by performing the asymmetric stabilization after the asymmetric induction, or one enantiomer of the second chiral molecule obtained by further performing the asymmetric stabilization on one enantiomer isolated by performing the isolation after the asymmetric induction. If the optically active substance according to an embodiment of the present invention is an optically active substance of the second chiral molecule, it is less likely to change to the other enantiomer of the second chiral molecule, providing stable optical activity. One enantiomer of the chiral molecule or one enantiomer of the second chiral molecule, which is the optically active substance according to an embodiment of the present invention, may co-exist with the other enantiomer of the chiral molecule or the other enantiomer of the second chiral molecule but has higher abundance than these other enantiomers because it is produced by the production method according to an embodiment of the present invention.

The enantiomeric excess of the optically active substance (one enantiomer) according to an embodiment of the present invention can be, for example, 40% ee or greater, 60% ee or greater, or 70% ee or greater, or all can be one enantiomer. Optically active substances having a great abundance of one enantiomer as such can effectively exhibit the function due to their asymmetry and are extremely useful as pharmaceuticals and various functional materials.

Method for Producing Chiral Molecule

Next, a method for producing a chiral molecule will be described.

The method for producing a chiral molecule according to an embodiment of the present invention includes allowing a reagent to act on a first chiral molecule having a half-life of enantiomeric excess of shorter than 10 hours at 50° C., of which one enantiomer is present in excess over the other enantiomer, thereby converting the first chiral molecule to a second chiral molecule having a longer half-life of enantiomeric excess (asymmetric stabilization).

According to this method for producing a chiral molecule, the first chiral molecule having a half-life of enantiomeric excess of shorter than 10 hours at 50° C. is converted to the second chiral molecule having a longer half-life of enantiomeric excess by allowing the reagent to act on the first chiral molecule, and thus an optically active substance of the first chiral molecule (optically active substance susceptible to racemization) can be converted to an optically active substance that is less susceptible to racemization while maintaining its optical purity. Thereby, an optically active substance having stable optical purity can be easily obtained.

For the description, scope, and specific examples of the first chiral molecule, reference can be made to the description, scope, and specific examples of the chiral molecule in the section of asymmetric induction in the above method for producing optically active substance. For the definition of the half-life of enantiomeric excess of the second chiral molecule, the description, scope, and specific examples of the reagent and the second chiral molecule, reference can be made to the definition of the half-life of enantiomeric excess of the second chiral molecule, the description, scope, and specific examples of the reagent and the second chiral molecule in the section of the asymmetric stabilization in the above method for producing optically active substance.

The "half-life of enantiomeric excess" of the first chiral molecule used in this asymmetric stabilization refers to the time until the initial enantiomeric excess of one enantiomer becomes ½ of the initial enantiomeric excess at a certain temperature, where the "one enantiomer" is the enantiomer (one enantiomer) present in excess in the first chiral molecule.

"One enantiomer is present in excess over the other enantiomer" in the first chiral molecule means that the enantiomeric excess of one enantiomer is greater than 0% ee, including also the case where the enantiomeric excess is 100% ee. That is, the first chiral molecule may include one enantiomer and the other enantiomer with a greater abundance of one enantiomer than that of the other enantiomer or may include only one enantiomer of one and the other enantiomers.

The enantiomeric excess of one enantiomer in the first chiral molecule can be, for example, 40% ee or greater, 70% ee or greater, or 100% ee or greater.

The first chiral molecule may be in any of a solid state, a liquid state, or a solution state. An additional component other than the first chiral molecule and the second chiral molecule may coexist as long as it does not adversely affect the conversion reaction from the first chiral molecule to the second chiral molecule.

The first chiral molecule may be obtained by any method but can be obtained by applying the method for producing an optically active substance according to an embodiment of the present invention. Specifically, the asymmetric induction is performed by allowing an asymmetry inducer to act on an optically active substance of a chiral molecule having a half-life of enantiomeric excess of shorter than 10 hours at 50° C. before the asymmetric stabilization, thereby increasing abundance of one enantiomer of the chiral molecule to obtain the first chiral molecule in which one enantiomer of the chiral molecule is present in excess over the other enantiomer, and the first chiral molecule obtained in this asymmetric induction can be used as the first chiral molecule in the asymmetric stabilization. Thereby, the first chiral molecule having a high enantiomeric excess of one enantiomer can be obtained by a simple operation under mild conditions at approximately room temperature. For the definition of the half-life of enantiomeric excess of the first chiral molecule, the first chiral molecule, the asymmetry inducer, and the method and conditions for allowing the asymmetry inducer to act on the first chiral molecule, reference can be made to the corresponding descriptions in the section of the asymmetric induction in the above method for producing optically active substance.

Chiral Molecule

The chiral molecule according to an embodiment of the present invention is produced by the method for producing a chiral molecule according to an embodiment of the present invention.

For the description, scope, and specific examples of the method for producing a chiral molecule according to an embodiment of the present invention, reference can be made to the contents described in the above section of method for producing chiral molecule. For the scope and specific examples of the chiral molecule according to an embodiment of the present invention, reference can be made to the scope and specific examples of the second chiral molecule in the section of asymmetric stabilization in the above method for producing optically active substance.

The chiral molecule according to an embodiment of the present invention is produced by the method for producing a chiral molecule according to an embodiment of the present invention, and thus an optically active substance can be obtained in which interconversion is less likely to occur between the enantiomers, and the enantiomeric excess is almost unchanged under mild temperature conditions (from 0 to 50° C.).

EXAMPLES

The characteristics of an embodiment of the present invention will be described more specifically with reference to synthesis examples and examples below. Materials, processing contents, processing procedures, and the like described below can be appropriately modified without departing from the spirit of the present invention. Accordingly, the scope of the present invention should not be construed as being limited by the specific examples described below.

Example 1: Production of Optically Active Substance Using 2.5 mg of Compound 1 as Chiral Molecule, Using Cellulose Tris(4-Methylbenzoate) as Asymmetry Inducer, and Using Dimethyldioxirane as Reagent (2.5 mg Scale Production Example)

Asymmetric Induction: 2.5 mg Scale

A diethyl ether solution (5 mL) of Compound 1 (2.5 mg) was prepared in a 20-mL round-bottom flask, 500 mg of silica gel by which cellulose tris(4-methylbenzoate) (asymmetry inducer) was supported was added and stirred, and then the solvent was distilled off using an evaporator. The resulting powder was transferred to a 1-mL sample tube, and 0.35 mL of a mixed solvent of cyclohexane and diisopropyl ether (10:1) was added and centrifuged to compress for 30 seconds. Thereafter, 0.25 mL of the same mixed solvent was further added, centrifuged to compress for 30 seconds, and the temperature was maintained at 25° C. using a heat block. After 24 hours, a gel was taken out of the sample tube to a filtering apparatus equipped with a polytetrafluoroethylene (PTFE) filter, washed with ice-cooled diethyl ether (21 mL), and filtered. The resulting filtrate was collected into an ice-cooled 100-mL round-bottom flask, and the enantiomeric excess of Compound 1 was measured by HPLC using a chiral stationary phase. Here, the measurement of the enantiomeric excess by HPLC was performed using CHIRALPAK AD-3 (available from Daicel Corporation, Φ4.6× 50 mm) and using ethanol as an eluent under the conditions of a flow rate of 0.5 mL/min, a column temperature of 10° C., and a detection wavelength λ of 254 nm. As a result of the measurement by HPLC, the enantiomeric excess of Compound 1 was 96% ee, achieving extremely high optical purity.

Asymmetric Induction: 20 mg Scale

A diethyl ether solution (40 mL) of Compound 1 (20 mg) was prepared in a 100-mL round-bottom flask, 4.0 g of silica gel by which cellulose tris(4-methylbenzoate) (asymmetry inducer) was supported was added and stirred, and then the solvent was distilled off using an evaporator. To the resulting powder, 2.0 mL of a mixed solvent of cyclohexane and diisopropyl ether (10:1) was added and mixed, and then the resulting mixture was transferred to a 15-mL sample tube pre-loaded with 1.8 mL of the same mixed solvent to allow precipitation to occur. Thereafter, to this mixture, 1.0 mL of the same mixed solvent was further added, and the temperature was maintained at 25° C. using an incubator. After 24 hours, a gel was taken out of the sample tube to a filtering apparatus equipped with a PTFE filter, washed with ice-cooled diethyl ether (84 mL), and filtered. The resulting filtrate was collected into an ice-cooled 100-mL round-bottom flask, and the enantiomeric excess of Compound 1 was measured by HPLC analysis using a chiral stationary phase. Here, the measurement of the enantiomeric excess by HPLC was performed under the same conditions as the HPLC analysis in the 2.5 mg scale asymmetric induction. The result of the measurement by HPLC shows that the enantiomeric excess of Compound 1 was 96% ee. From this, it was found that the production method according to an embodiment of the present invention can achieve high enantiomeric excess regardless of the scale and is also suitable for large-scale industrialization.

Asymmetric Stabilization: Epoxidation

[Chem. 34]

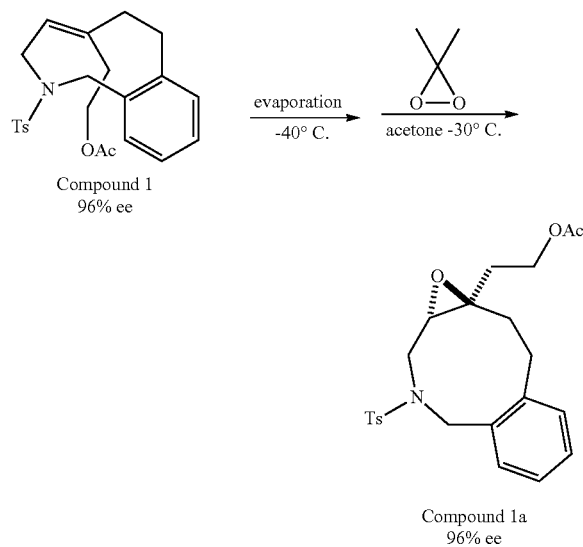

Compound 1
96% ee

Compound 1a
96% ee

The solution of Compound 1 after the asymmetric induction was stirred at −40° C. under reduced pressure using an oil rotary vacuum pump to distill off the solvent. The resulting colorless amorphous Compound 1 was cooled to −78° C., an acetone solution of dimethyldioxirane (reagent) (0.055 M, 2.8 mL) was added, and then the temperature was slowly raised to −30° C. under stirring. After 3 hours, the solvent was distilled off from this reaction solution at −30° C., dichloromethane (10 mL) and a saturated aqueous solution of sodium thiosulfate (10 mL) were added, and the mixture was transferred to a separatory funnel. The organic phase was separated, then the aqueous phase was extracted with dichloromethane (2×10 mL), the combined organic phase was washed with a saturated salt solution (10 mL) and then dried with sodium sulfate. The organic phase after drying was filtered through a cotton plug, and then the solvent was distilled off with an evaporator. The resulting concentrate was purified by silica gel column chromatography using a mixed solvent of hexane:ethyl acetate=2:1 as an eluent, and the peak fraction thereof was concentrated to obtain 19.6 mg of Compound 1a as a colorless crystal, with a yield of 89%. The enantiomeric excess was measured for the resulting Compound 1a by HPLC using a chiral stationary phase. Here, the measurement of the enantiomeric excess by HPLC was performed using CHIRALPAK AD-3 (available from Daicel Corporation, Φ4.6×250 mm) and using a mixed solvent of hexane:ethanol=50:50 as an eluent under the conditions of a flow rate of 0.5 mL/min, a column temperature of 25° C., and a detection wavelength λ of 254 nm. Compound 1a had an enantiomeric excess of 96% ee, having the same enantiomeric excess as Compound 1 after the asymmetric induction. From this, it was found that by performing the asymmetric stabilization, an optically active substance is obtained while maintaining the enantiomeric excess.

Asymmetric Stabilization: aza[2,3] Rearrangement

[Chem. 35]

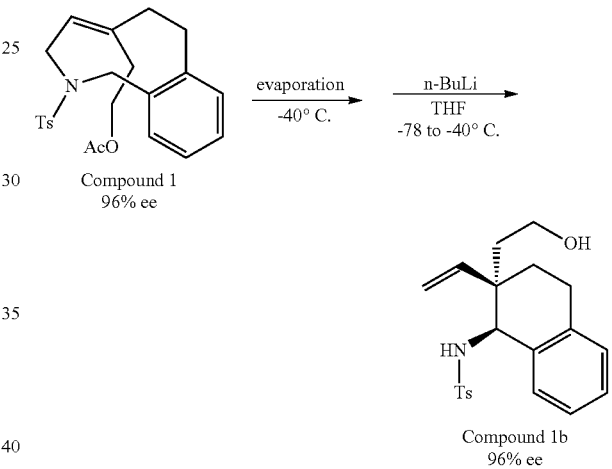

Compound 1
96% ee

Compound 1b
96% ee

The solution of Compound 1 after the asymmetric induction was stirred at −40° C. under reduced pressure using an oil rotary vacuum pump to distill off the solvent. The resulting colorless amorphous Compound 1 was dissolved in THF at −78° C., a hexane solution of n-butyllithium (reagent) (1.46 M, 0.662 mL) was added, and then the temperature was slowly raised to −40° C. under stirring. After 2.5 hours, a saturated aqueous solution of ammonium chloride and ethyl acetate were added to this reaction solution, the temperature was raised to room temperature, and then the mixture was transferred to a separatory funnel. The organic phase was separated, then the aqueous phase was extracted with ethyl acetate (2×10 mL), the combined organic phase was washed with a saturated salt solution (10 mL) and then dried with sodium sulfate. The organic phase after drying was filtered through a cotton plug, and then the solvent was distilled off with an evaporator. The resulting concentrate was purified by silica. gel column chromatography using a mixed solvent of hexane:ethyl acetate=1:1 as an eluent, and the peak fraction thereof was concentrated to obtain 11.2 mg of Compound 1b as a colorless crystal, with a yield of 62%. The enantiomeric excess was measured for the resulting Compound 1b by HPLC using a chiral stationary phase. Here, the measurement of the enantiomeric excess by HPLC was performed using CHIRALPAK AD-H (available from Daicel Corporation, Φ4.6×250 mm) and using a mixed solvent of hexane:ethanol=70:30 as an eluent under the conditions of a flow rate of 0.5 mL/min, a column temperature of 20° C., and a detection wavelength λ of 254 nm. Compound 1b had an enantiomeric excess of 96% ee, having the same enantiomeric excess as Compound 1 after the asymmetric induction.

Example 2: Production of Optically Active Substance Using Compound 2 as Chiral Molecule, Using Cellulose tris(4-methylbenzoate) as Asymmetry Inducer, and Using Dimethyldioxirane as Reagent Asymmetric Induction: 2.5 mg Scale A diethyl ether solution (5 mL) of Compound 2 (2.5 mg) was prepared in a 20-mL round-bottom flask, 500 mg of silica gel by which cellulose tris(4-methylbenzoate) (asymmetry inducer) was supported was added and stirred, and then the solvent was distilled off using an evaporator. The resulting powder was transferred to a 1-mL sample tube, and 0.35 mL of a mixed solvent of cyclohexane and diisopropyl ether (10:1) was added and centrifuged to compress for 30 seconds. Thereafter, 0.25 mL of the same mixed solvent was further added, centrifuged to compress for 30 seconds, and the temperature was maintained at 25° C. using a heat block. After 24 hours, a gel was taken out of the sample tube to a filtering apparatus equipped with a polytetrafluoroethylene (PTFE) filter, washed with ice-cooled diethyl ether (21 mL), and filtered. The resulting filtrate was collected into an ice-cooled 100-mL round-bottom flask, and the enantiomeric excess of Compound 2 was measured by high performance liquid chromatography (HPLC) using a chiral stationary phase. Here, the measurement of the enantiomeric excess by HPLC was performed using CHIRALPAK AD-3 (available from Daicel Corporation, Φ4.6×50 mm) and using ethanol as an eluent under the conditions of a flow rate of 0.5 mL/min, a column temperature of 10° C., and a detection wavelength λ of 254 nm. The result of the measurement by HPLC shows that the enantiomeric excess of Compound 2 was 94% ee.

Asymmetric Induction: 20 mg Scale

A diethyl ether solution (40 mL) of Compound 2 (20 mg) was prepared in a 100-mL round-bottom flask, 4.0 g of silica gel by which cellulose tris(4-methylbenzoate) (asymmetry inducer) was supported was added and stirred, and then the solvent was distilled off using an evaporator. To the resulting powder, 2.0 mL of a mixed solvent of cyclohexane and diisopropyl ether (10:1) was added and mixed, and then the resulting mixture was transferred to a 15-mL sample tube pre-loaded with 1.8 mL of the same mixed solvent to allow precipitation to occur. Thereafter, to this mixture, 1.0 mL of the same mixed solvent was further added, and the temperature was maintained at 25° C. using an incubator. After 24 hours, a gel was taken out of the sample tube to a filtering apparatus equipped with a PTFE filter, washed with ice-cooled diethyl ether (84 mL), and filtered. The resulting filtrate was collected into an ice-cooled 100-mL round-bottom flask, and the enantiomeric excess of Compound 2 was measured by HPLC analysis using a chiral stationary phase. Here, the measurement of the enantiomeric excess by HPLC was performed under the same conditions as the HPLC analysis in the 2.5 mg scale asymmetric induction. The result of the measurement by HPLC shows that the enantiomeric excess of Compound 2 was 96% ee.

Asymmetric Stabilization

[Chem. 36]

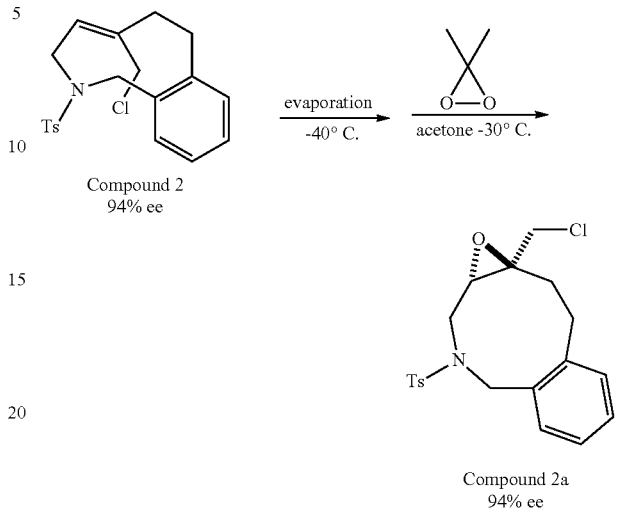

Compound 2
94% ee

Compound 2a
94% ee

Asymmetric Stabilization

The solution of Compound 2 after the asymmetric induction was stirred at −40° C. under reduced pressure using an oil rotary vacuum pump to distill off the solvent. The resulting colorless amorphous Compound 2 was cooled to −78° C., an acetone solution of dimethyldioxirane (reagent) (0.055 M, 2.9 mL) was added, and then the temperature was slowly raised to −30° C. under stirring. After 4 hours, the solvent was distilled off from this reaction solution at −30° C., dichloromethane (10 mL) and a saturated aqueous solution of sodium thiosulfate (10 mL) were added, and the mixture was transferred to a separatory funnel. The organic phase was separated, then the aqueous phase was extracted with dichloromethane (2×10 mL), the combined organic phase was washed with a saturated salt solution (10 mL) and then dried with sodium sulfate. The organic phase after drying was filtered through a cotton plug, and then the solvent was distilled off with an evaporator. The resulting concentrate was purified by silica gel column chromatography using a mixed solvent of hexane:ethyl acetate=5:1 as an eluent, and the peak fraction thereof was concentrated to obtain 18.0 mg of Compound 2a as a colorless crystal, with a yield of 83%. The enantiomeric excess was measured for the resulting Compound 2a by HPLC using a chiral stationary phase. Here, the measurement of the enantiomeric excess by HPLC was performed using CHIRALPAK AD-H (available from Daicel Corporation, Φ4.6×250 mm) and using a mixed solvent of hexane:2-propanol=50:50 as an eluent under the conditions of a flow rate of 0.5 mL/min, a column temperature of 25° C., and a detection wavelength λ of 254 nm. Compound 2a had an enantiomeric excess of 94% ee, having the same enantiomeric excess as Compound 2 after the asymmetric induction.

Example 3: Production of Optically Active Substance Using Compound 3 as Chiral Molecule, Using Amylose tris(3,5-dimethylphenylcarbamate) as Asymmetry Inducer, and Using iPrMgCl.LiCl as Reagent Asymmetric Induction: 2.5 mg Scale A diethyl ether solution (5 mL) of Compound 3 (2.5 mg) was prepared in a 20-mL round-bottom flask, 500 mg of silica gel by which amylose tris(3,5-dimethylphenylcarbamate) was supported was added and stirred, and then the solvent was distilled off using an evaporator. The resulting powder was transferred to a 1-mL sample tube, and 0.35 mL of a mixed solvent of cyclohexane and ethanol (10:1) was added and centrifuged to compress for 30 seconds. Thereafter, 0.25 mL of the same mixed solvent was further added, centrifuged to compress for 30 seconds, and the temperature was maintained at 25° C. using a heat block. After 168 hours, a gel was taken out of the sample tube to a filtering apparatus equipped with a polytetrafluoroethylene (PTFE) filter, washed with ice-cooled diethyl ether (21 mL), and filtered. The resulting filtrate was collected into an ice-cooled 100-mL round-bottom flask, and the enantiomeric excess of Compound 3 was measured by high performance liquid chromatography (HPLC) using a chiral stationary phase. Here, the measurement of the enantiomeric excess by HPLC was performed using CHIRALPAK AS-3 (available from Daicel Corporation, Φ4.6×50 mm) and using a mixed solvent of hexane and ethanol (4:1) as an eluent under the conditions of a flow rate of 1.0 mL/min, a column temperature of 15° C., and a detection wavelength λ of 254 nm. The result of the measurement by HPLC shows that the enantiomeric excess of Compound 3 was 81% ee, achieving extremely high enantiomeric excess.

Asymmetric Induction: 20 mg Scale

A diethyl ether solution (40 mL) of Compound 3 (20 mg) was prepared in a 100-mL round-bottom flask, 4.0 g of silica gel by which amylose tris(3,5-dimethylphenylcarbamate) (asymmetry inducer) was supported was added and stirred, and then the solvent was distilled off using an evaporator. To the resulting powder, 2.0 mL of a mixed solvent of cyclohexane and diisopropyl ether (10:1) was added and mixed, and then the resulting mixture was transferred to a 15-mL sample tube pre-loaded with 1.8 mL of the same mixed solvent to allow precipitation to occur. Thereafter, to this mixture, 1.0 mL of the same mixed solvent was further added, and the temperature was maintained at 25° C. using an incubator. After 192 hours, a gel was taken out of the sample tube to a filtering apparatus equipped with a PTFE filter, washed with ice-cooled diethyl ether (84 mL), and filtered. The resulting filtrate was collected into an ice-cooled 100-mL round-bottom flask, and the enantiomeric excess of Compound 3 was measured by HPLC analysis using a chiral stationary phase. Here, the measurement of the enantiomeric excess by HPLC was performed under the same conditions as the HPLC analysis in the 2.5 mg scale asymmetric induction. The result of the measurement by HPLC shows that the enantiomeric excess of Compound 3 was 81% ee.

Asymmetric Stabilization

[Chem. 37]

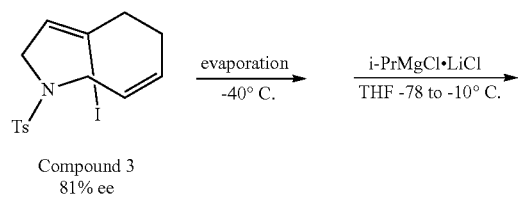

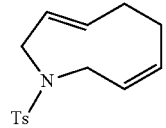

Compound 3a
81% ee

The solution of Compound 3 after the asymmetric induction was stirred at −40° C. under reduced pressure using an oil rotary vacuum pump to distill off the solvent. A tetrahydrofuran solution (5 mL) of the resulting colorless amorphous Compound 3 (23.0 mg, 0.0570 mmol, 81% ee) was cooled to −78° C., iPrMgCl·LiCl (reagent) was added, and then the temperature was slowly raised to −10° C. under stirring. After 30 minutes, a saturated aqueous solution of ammonium chloride was added to stop the reaction, and the mixture was extracted with ethyl acetate. The organic phase was washed with a saturated salt solution and then dried with sodium sulfate. The organic phase after drying was filtered through a cotton plug, and then the solvent was distilled off with an evaporator. The resulting concentrate was purified by silica gel column chromatography using a mixed solvent of hexane:ethyl acetate=10:1 as an eluent, and the peak fraction thereof was concentrated to obtain 11.4 mg of Compound 3a as a colorless crystal, with a yield of 88%. The enantiomeric excess was measured for the resulting Compound 3a by HPLC using a chiral stationary phase. Here, the measurement of the enantiomeric excess by HPLC was performed using CHIRALPAK IB (available from Daicel Corporation, Φ4.6×250 mm) and using a mixed solvent of hexane:isopropanol=80:20 as an eluent under the conditions of a flow rate of 0.5 mL/min, a column temperature of 25° C., and a detection wavelength λ of 254 nm. Compound 3a had an enantiomeric excess of 81% ee, having the same enantiomeric excess as Compound 3 after the asymmetric induction. From this, it was found that by performing the asymmetric stabilization, an optically active substance is obtained while maintaining the enantiomeric excess.

Example 4: Production of Optically Active Substance Using Compound 4 as Chiral Molecule and Using Cellulose tris(4-methylbenzoate) as Asymmetry Inducer Asymmetric Induction: 2.5 mg Scale A diethyl ether solution (5 mL) of Compound 4 (2.5 mg) was prepared in a 20-mL round-bottom flask, 500 mg of silica gel by which cellulose tris(4-methylbenzoate) (asymmetry inducer) was supported was added and stirred, and then the solvent was distilled off using an evaporator. The resulting powder was transferred to a 1-mL sample tube, and 0.35 mL of a mixed solvent of cyclohexane and diethyl ether (10:1) was added and centrifuged to compress for 30 seconds. Thereafter, 0.25 mL of the same mixed solvent was further added, centrifuged to compress for 30 seconds, and the temperature was maintained at 25° C. using a heat block. After 24 hours, a gel was taken out of the sample tube to a filtering apparatus equipped with a polytetrafluoroethylene (PTFE) filter, washed with ice-cooled diethyl ether (21 mL), and filtered. The resulting filtrate was collected into an ice-cooled 100-mL round-bottom flask, and the enantiomeric excess of Compound 4 was measured by high performance liquid chromatography (HPLC) using a chiral stationary phase. Here, the measurement of the enantiomeric excess by HPLC was performed using CHIRAL CEL OD-3 (available from Daicel Corporation, Φ4.6×50 mm) and using a mixed solvent of hexane and ethanol (4:1) as an eluent under the conditions of a flow rate of 0.5 mL/min, a column temperature of 10° C., and a detection wavelength λ of 254 nm. The result of the measurement by HPLC shows that the enantiomeric excess of Compound 4 was 59% ee.

Examples 5 to 9

The asymmetric induction was performed in the same manner as in Example 1 except for using Compounds 5 to 9 instead of Compound 1 and the asymmetry inducer shown in Table 1. All the asymmetric inductions were successful. The measurement results of the enantiomeric excesses for Compounds 7 and 9 after the asymmetric induction are shown in Table 1.

Example 10: Production of Optically Active Substance Using Compound 10 as Chiral Molecule, Using Amylose tris(3,5-dimethylphenylcarbamate) as Asymmetry Inducer, and Using m-Chloroperbenzoic Acid and Trimethylaluminum as Reagents Asymmetric Induction: 2.5 mg Scale A diethyl ether solution (5 mL) of Compound 10 (2.5 mg) was prepared in a 20-mL round-bottom flask, 500 mg of silica gel by which amylose tris(3,5-dimethylphenylcarbamate) (asymmetry inducer) was supported was added and stirred, and then the solvent was distilled off using an evaporator. The resulting powder was transferred to a 1-mL sample tube, and 0.35 mL of cycloheptane was added and centrifuged to compress for 30 seconds. Thereafter, 0.25 mL of the same mixed solvent was further added, centrifuged to compress for 30 seconds, and the temperature was maintained at 25° C. using a heat block. After 24 hours, a gel was taken out of the sample tube to a filtering apparatus equipped with a polytetrafluoroethylene (PTFE) filter, washed with ice-cooled diethyl ether (21 mL), and filtered. The resulting filtrate was collected into an ice-cooled 100-mL round-bottom flask, and the enantiomeric excess of Compound 10 was measured by high performance liquid chromatography (HPLC) using a chiral stationary phase. Here, the measurement of the enantiomeric excess by HPLC was performed using CHIRALPAK AD-3 (available from Daicel Corporation, Φ4.6×50 mm) and using a mixed solvent of hexane and 2-propanol (9:1) as an eluent under the conditions of a flow rate of 0.5 mL/min, a column temperature of 20° C., and a detection wavelength λ of 254 nm. The result of the measurement by HPLC shows that the enantiomeric excess of Compound 10 was 76% ee.

Asymmetric Induction: 20 mg Scale

A diethyl ether solution (40 mL) of Compound 10 (20 mg) was prepared in a 100-mL round-bottom flask, 4.0 g of silica gel by which amylose tris(3,5-dimethylphenylcarbamate) (asymmetry inducer) was supported was added and stirred, and then the solvent was distilled off using an evaporator. To the resulting powder, 2.0 mL of cyclopentane was added and mixed, and then the resulting mixture was transferred to a 15-mL sample tube pre-loaded with 1.8 mL of the same solvent to allow precipitation to occur. Thereafter, to this mixture, 1.0 mL of the same mixed solvent was further added, and the temperature was maintained at 25° C. using an incubator. After 24 hours, a gel was taken out of the sample tube to a filtering apparatus equipped with a PTFE filter, washed with ice-cooled diethyl ether (84 mL), and filtered. The resulting filtrate was collected into an ice-cooled 100-mL round-bottom flask, and the enantiomeric excess of Compound 10 was measured by HPLC analysis using a chiral stationary phase. Here, the measurement of the enantiomeric excess by HPLC was performed using CHIRALPAK AD-3 (available from Daicel Corporation, Φ4.6× 250 mm) and using a mixed solvent of hexane and 2-propanol (9:1) as an eluent under the conditions of a flow rate of 0.7 mL/min, a column temperature of 10° C., and a detection wavelength λ of 254 nm. The result of the measurement by HPLC shows that the enantiomeric excess of Compound 10 was 76% ee.

Asymmetric Stabilization: Epoxidation, Epoxy Ring Opening

[Chem. 38]

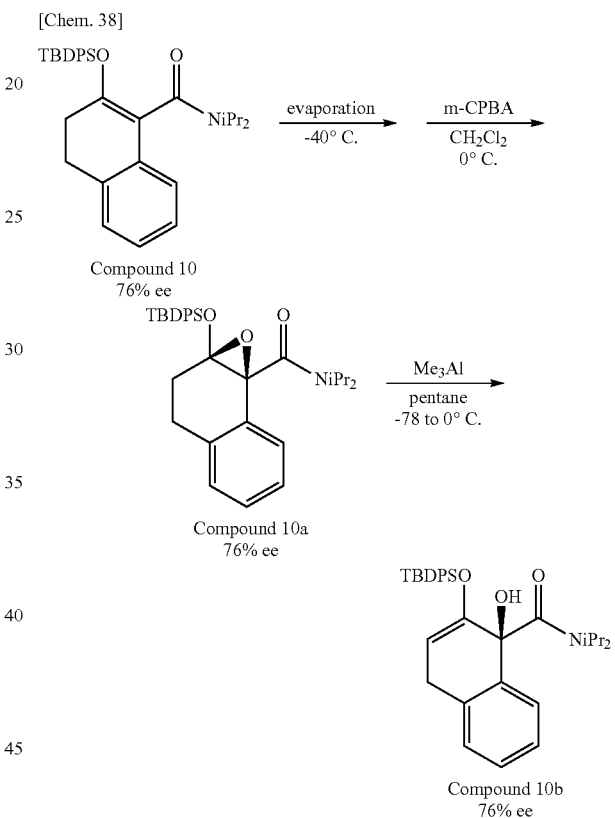

Compound 10
76% ee

Compound 10a
76% ee

Compound 10b
76% ee

The solution of Compound 10 after the asymmetric induction was stirred at −40° C. under reduced pressure using an oil rotary vacuum pump to distill off the solvent. A dichloromethane solution (5 mL) of the resulting colorless amorphous Compound 10 (20.0 mg, 0.0391 mmol, 76% ee) was cooled to 0° C., m-chloroperbenzoic acid (about 70%, 62.0 mg) (reagent) was added and stirred for 1 hour. A saturated aqueous solution of sodium thiosulfate was added to stop the reaction, and the mixture was extracted with diethyl ether. The organic phase was washed with a saturated aqueous solution of sodium hydrogen carbonate and a saturated salt solution and then dried with sodium sulfate. The organic phase after drying was filtered through a cotton plug, and then the solvent was distilled off with an evaporator. The resulting concentrate was dissolved in pentane (5 mL), trimethylaluminum (1.08 M, 0.2 mL) was added at −78° C., and then the temperature was raised to 0° C. under stirring. After 20 minutes, methanol and potassium sodium tartrate were added and stirred for 30 minutes. Water was added, then the aqueous phase was extracted with ethyl acetate, and the combined organic phase was washed with saturated salt solution (10 mL) and then dried with sodium sulfate. The organic phase after drying was filtered through a cotton plug, and then the solvent was distilled off with an evaporator. The resulting concentrate was purified by silica gel column chromatography using a mixed solvent of hexane:ethyl acetate=3:1 as an eluent, and the peak fraction thereof was concentrated to obtain 17.7 mg of Compound 10b as a white crystal, with a yield of 86%. The enantiomeric excess was measured for the resulting Compound 10b by HPLC using a chiral stationary phase. Here, the measurement of the enantiomeric excess by HPLC was performed using CHIRALPAK IG (available from Daicel Corporation, Φ4.6×250 mm) and using a mixed solvent of hexane:isopropanol=95:5 as an eluent under the conditions of a flow rate of 0.5 mL/min, a column temperature of 25° C., and a detection wavelength λ of 254 nm. Compound 10b had an enantiomeric excess of 76% ee, having the same enantiomeric excess as Compound 10 after the asymmetric induction. From this, it was found that by performing the asymmetric stabilization, an optically active substance is obtained while maintaining the enantiomeric excess.

Examples 11 to 17: Production of Optically Active Substance Using Compounds 11 to 17 as Chiral Molecules, Using Cellulose tris(3,5-dimethylphenylcarbamate) as Asymmetry Inducer, and Using Ethanol and Lithium Hydroxide as Reagents The asymmetric induction was performed in the same manner as in Example 1 except for using Compounds 11 to 17 instead of Compound 1 and using cellulose tris(3,5-dimethylphenylcarbamate) as the asymmetry inducer. All the asymmetric inductions were successful. The measurement results of the enantiomeric excesses for Compounds 11 and 13 to 17 after the asymmetric induction are shown in Table 1. The asymmetric induction of Compound 17 is specifically described below as a representative example.

Asymmetric Induction: 2.5 mg Scale

A diethyl ether solution (5 mL) of Compound 17 (2.5 mg) was prepared in a 20-mL round-bottom flask, 500 mg of silica gel by which amylose tris(3,5-dimethylphenylcarbamate) (asymmetry inducer) was supported was added and stirred, and then the solvent was distilled off using an evaporator. The resulting powder was transferred to a 1-mL sample tube, and 0.35 mL of a mixed solvent of hexane and diisopropyl ether (10:1) was added and centrifuged to compress for 30 seconds. Thereafter, 0.25 mL of the same mixed solvent was further added, centrifuged to compress for 30 seconds, and the temperature was maintained at 25° C. using a heat block. After 24 hours, a gel was taken out of the sample tube to a filtering apparatus equipped with a polytetrafluoroethylene (PTFE) filter, washed with ice-cooled ethanol (21 mL), and filtered. The resulting filtrate was collected into an ice-cooled 100-mL round-bottom flask, and the enantiomeric excess of Compound 17 was measured by high performance liquid chromatography (HPLC) using a chiral stationary phase. Here, the measurement of the enantiomeric excess by HPLC was performed using CHIRAL CEL OD-3 (available from Daicel Corporation, Φ4.6×50 mm) and using a mixed solvent of hexane and ethanol (4:1) as an eluent under the conditions of a flow rate of 0.5 mL/min, a column temperature of 15° C., and a detection wavelength λ of 254 nm. The result of the measurement by HPLC shows that the enantiomeric excess of Compound 17 was 92% ee.

Asymmetric Induction: 20 mg Scale

A diethyl ether solution (40 mL) of Compound 17 (20 mg) was prepared in a 100-mL round-bottom flask, 4.0 g of silica gel by which amylose tris(3,5-dimethylphenylcarbamate) (asymmetry inducer) was supported was added and stirred, and then the solvent was distilled off using an evaporator. To the resulting powder, 2.0 mL of a mixed solvent of hexane and diisopropyl ether (10:1) was added and mixed, and then the resulting mixture was transferred to a 15-mL sample tube pre-loaded with 1.8 mL of the same mixed solvent to allow precipitation to occur. Thereafter, to this mixture, 1.0 mL of the same mixed solvent was further added, and the temperature was maintained at 25° C. using an incubator. After 24 hours, a gel was taken out of the sample tube to a filtering apparatus equipped with a PTFE filter, washed with ice-cooled ethanol (84 mL), and filtered. The resulting filtrate was collected into an ice-cooled 100-mL round-bottom flask, and the enantiomeric excess of Compound 17 was measured by HPLC analysis using a chiral stationary phase. Here, the measurement of the enantiomeric excess by HPLC was performed under the same conditions as the HPLC analysis in the 2.5 mg scale asymmetric induction. The result of the measurement by HPLC shows that the enantiomeric excess of Compound 17 was 92% ee.

Asymmetric Stabilization: Solvolysis

[Chem. 39]

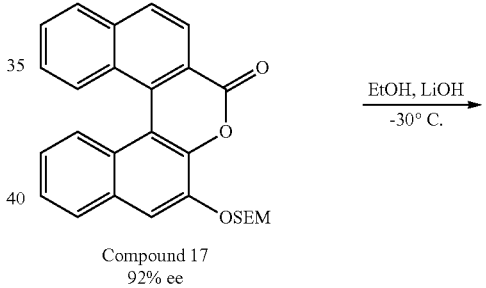

Compound 17
92% ee

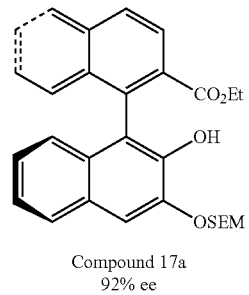

Compound 17a
92% ee

An ethanol solution (82 mL) of Compound 17 (20.0 mg, 0.0452 mmol, 92% ee) after the asymmetric induction was cooled to −30° C., lithium hydroxide (21.6 mg, 0.904 mmol) (reagent) was added and stirred for 15 minutes, and then the solvent was distilled off with an evaporator to a remaining volume of approximately 0.5 mL. The resulting concentrate was purified by silica gel column chromatography using a mixed solvent of hexane:ethyl acetate=3:1 as an eluent, and the peak fraction thereof was concentrated to obtain 19.1 mg of Compound 17a as a colorless crystal, with a yield of 86%. The enantiomeric excess was measured for the resulting compound by HPLC using a chiral stationary phase. Here, the measurement of the enantiomeric excess by HPLC was performed using CHIRALPAK AS-H (available from Daicel Corporation, Φ4.6×250 mm) and using a mixed solvent of hexane:isopropanol=9:1 as an eluent under the conditions of a flow rate of 0.5 mL/min, a column temperature of 25° C., and a detection wavelength λ of 254 nm. Compound 17a had an enantiomeric excess of 92% ee, having the same enantiomeric excess as Compound 17 after the asymmetric induction. From this, it was found that by performing the asymmetric stabilization, an optically active substance is obtained while maintaining the enantiomeric excess.

All the chiral molecules used in the examples had a half-life of enantiomeric excess of shorter than 10 hours at 50° C. In addition, the asymmetric induction was successful in each example. The measurement results of the enantiomeric excesses of the compounds obtained in Examples 1 to 4, 7, 9 to 11, and 13 to 17 are summarized in Table 1.

The NMR data of the new compounds synthesized in the above examples are described below.

[Chem. 40]

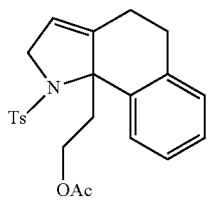

Compound 1

$^1$H NMR (300 MHz, CDCl$_3$): δ 7.77 (d, J=8.1 Hz, 2H), 7.67 (d, J=7.2 Hz, 1H), 7.38 (d, J=8.1 Hz, 2H), 7.30-7.20 (m, 2H), 7.07 (d, J=7.5 Hz, 1H), 4.59 (dd, J=11.6, 5.4 Hz, 1H), 4.53 (d, J=14.1 Hz, 1H), 4.08-3.93 (m, 3H), 3.61 (dd, J=11.1, 10.8 Hz, 1H), 3.10 (d, J=14.1 Hz, 1H), 2.80-2.74 (m, 1H), 2.52-2.38 (m, 2H), 2.47 (s, 3H), 2.25-2.16 (m, 1H), 2.00 (s, 3H), 2.03-1.91 (m, 1H), 1.83 (dd, J=13.2, 11.4 Hz, 1H).

$^{13}$C NMR (75 MHz, CDCl$_3$): δ 170.8, 143.4, 141.2, 139.7, 137.8, 135.1, 131.2, 131.1, 129.9, 128.0, 127.4, 127.3, 122.8, 62.6, 46.3, 45.7, 38.8, 32.9, 29.9, 21.7, 21.0.

TABLE 1

| Example No. | Chiral molecule | Asymmetry inducer | Enantiometric excess after asymmetric induction | Asymmetric stabilizer | Compound obtained in asymmetric stabilization | Enantiomeric excess after asymmetric stabilization |
|---|---|---|---|---|---|---|
| Example 1 | Compound 1 | Cellulose tris(4-methylbenzoate) | 96% ee | Dimethyldioxirane | Compound 1a | 96% ee |
| | | | | | Compound 1b | 96% ee |
| Example 2 | Compound 2 | Cellulose tris(4-methylbenzoate) | 94% ee | n-butyllithium | Compound 2a | 94% ee |
| | | | | | Compound 2b | 94% ee |
| Example 3 | Compound 3 | Amylose tris(3,5-dimethylphenylcarbamate) | 81% ee | iPrMgCl•LiCl | Compound 3a | 81% ee |
| Example 4 | Compound 4 | Cellulose tris(4-methylbenzoate) | 59% ee | | | |
| Example 5 | Compound 5 | Cellulose tris(3,5-dimethylphenylcarbamate) | Asymmetric induction successful | | | |
| Example 6 | Compound 6 | Cellulose tris(4-methylbenzoate) | Asymmetric induction successful | | | |
| Example 7 | Compound 7 | Amylose tris{(S)-α-methylbenzylcarbamate} | 75% ee | | | |
| Example 8 | Compound 8 | Amylose tris(3,5-dimethylphenylcarbamate) | Asymmetric induction successful | | | |
| Example 9 | Compound 9 | Amylose tris(3,5-dimethylphenylcarbamate) | 68% ee | | | |
| Example 10 | Compound 10 | Amylose tris(3,5-dimethylphenylcarbamate) | 76% ee | m-chloroperbenzoic acid, Trimethylaluminum | Compound 10a | 76% ee |
| | | | | | Compound 10b | 76% ee |
| Example 11 | Compound 11 | Cellulose tris(3,5-dimethylphenylcarbamate) | 50% ee | | | |
| Example 12 | Compound 12 | Cellulose tris(3,5-dimethylphenylcarbamate) | Asymmetric induction successful | | | |
| Example 13 | Compound 13 | Cellulose tris(3,5-dimethylphenylcarbamate) | 81% ee | | | |
| Example 14 | Compound 14 | Cellulose tris(3,5-dimethylphenylcarbamate) | 85% ee | | | |
| Example 15 | Compound 15 | Cellulose tris(3,5-dimethylphenylcarbamate) | 79% ee | | | |
| Example 16 | Compound 16 | Cellulose tris(3,5-dimethylphenylcarbamate) | 86% ee | | | |
| Example 17 | Compound 17 | Cellulose tris(3,5-dimethylphenylcarbamate) | 92% ee | Ethanol, lithium hydroxide | Compound 17a | 92% ee |

[Chem. 41]

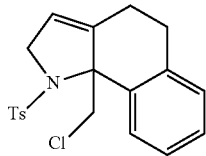

Compound 2

¹H NMR (300 MHz, CDCl₃): δ 7.76 (d, J=8.4 Hz, 2H), 7.68 (d, J=7.5 Hz, 1H), 7.39 (d, J=8.4 Hz, 2H), 7.32-7.12 (m, 2H), 7.09 (dd, J=7.4, 1.4 Hz, 1H), 4.72 (dd, J=11.6, 5.4 Hz, 1H), 4.58 (d, J=14.0 Hz, 1H), 4.03 (dd, J=10.8, 5.4 Hz, 1H), 3.84 (d, J=12.0 Hz, 1H), 3.80 (d, J=12.0 Hz, 1H), 3.59 (dd, J=11.6, 10.8 Hz, 1H), 3.16 (d, J=14.0 Hz, 1H), 2.83 (ddd, J=13.6, 4.9, 2.3 Hz, 1H), 2.71 (ddd, J=12.3, 4.9, 1.8 Hz, 1H), 2.58 (dd, J=13.6, 13.4 Hz, 1H), 2.48 (s, 3H), 1.92 (dd, J=13.4, 12.3 Hz, 1H).

¹³C NMR (75 MHz, CDCl₃): δ 143.8, 140.0, 139.3, 137.8, 131.3, 131.2, 130.0, 128.3, 127.5, 127.3, 125.4, 46.7, 45.8, 41.8, 37.2, 33.6, 21.7.

[Chem. 42]

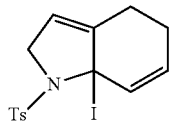

Compound 3

¹H NMR (300 MHz, CDCl₃): δ 7.70 (d, J=8.4 Hz, 2H), 7.33 (d, J=8.4 Hz, 2H), 5.79 (ddd, J=11.4, 11.4, 4.8 Hz, 1H), 5.45 (dd, J=10.5, 4.8 Hz, 1H), 5.44-5.38 (m, 1H), 4.44 (dd, J=10.8, 4.8 Hz, 1H), 3.87 (dd, J=14.1, 4.8 Hz, 1H), 3.42 (dd, J=10.8, 10.5 Hz, 1H), 2.97 (dd, J=14.1, 11.4 Hz, 1H), 2.76-2.69 (m, 1H), 2.44 (s, 3H), 2.34-2.25 (m, 1H), 2.13-2.06 (m, 2H).

¹³C NMR (75 MHz, CDCl₃): δ 143.3, 135.5, 134.2, 132.5, 129.7, 127.2, 126.7, 116.1, 55.3, 45.1, 45.0, 26.3, 21.7.

[Chem. 43]

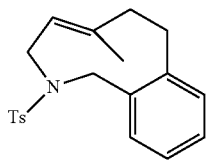

Compound 4

¹H NMR (300 MHz, CDCl₃): δ 7.77 (d, J=8.0 Hz, 2H), 7.69 (d, J=7.5 Hz, 1H), 7.36 (d, J=8.0 Hz, 2H), 7.29-7.18 (m, 2H), 7.06 (d, J=7.2 Hz, 1H), 4.54 (d, J=14.0 Hz, 1H), 4.52-4.47 (m, 1H), 3.95 (dd, J=10.5, 5.4 Hz, 1H), 3.55 (dd, J=10.8, 10.5 Hz, 1H), 3.07 (d, J=14.0 Hz, 1H), 2.74 (ddd, J=13.7, 5.1, 2.1 Hz, 1H), 2.52-2.43 (m, 1H), 2.46 (s, 3H), 2.36 (ddd, J=11.7, 5.1, 1.5 Hz, 1H), 1.89 (ddd, J=11.7, 10.5, 1.5 Hz, 1H), 1.49 (s, 3H).

¹³C NMR (75 MHz, CDCl₃): δ 143.3, 141.4, 140.1, 138.4, 135.1, 131.0, 131.0, 129.8, 127.7, 127.4, 127.1, 120.4, 46.4, 46.3, 40.9, 32.7, 21.6, 17.3.

[Chem. 44]

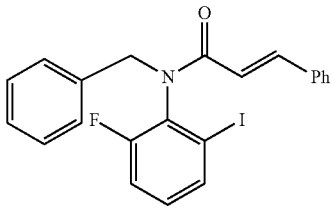

Compound 5

¹H NMR (300 MHz, CDCl₃): δ 7.83 (d, J=15.3 Hz, 1H), 7.73 (ddd, J=3.6, 3.6, 1.2 Hz, 1H), 7.36-7.23 (m, 10H), 7.11-7.04 (m, 2H), 6.12 (dd, J=15.6, 0.6 Hz, 1H), 5.33 (d, J=14.1 Hz, 1H), 4.66 (d, J=14.1 Hz, 1H).

¹³C NMR (100 MHz, CDCl₃): δ 165.9, 158.9 (d, $J_{C-F}$=254 Hz), 143.8, 136.0, 135.5 (d, $J_{C-F}$=3.8 Hz), 135.0, 132.1 (d, $J_{C-F}$=14.4 Hz), 131.3 (d, $J_{C-F}$=8.6 Hz), 130.1, 129.8, 128.7, 128.2, 128.0, 127.8, 117.6, 116.8 (d, $J_{C-F}$=21.1 Hz), 102.0, 51.7.

[Chem. 45]

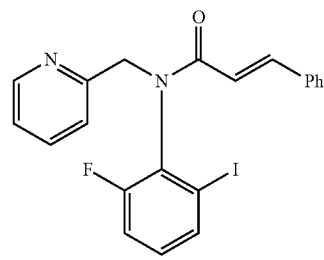

Compound 6

¹H NMR (300 MHz, CDCl₃): δ 8.33 (ddd, J=4.8, 1.5, 1.5 Hz, 1H), 7.74 (d, J=15.6 Hz, 1H), 7.68-7.56 (m, 3H), 7.26-7.19 (m, 5H), 7.09 (ddd, J=7.5, 5.1, 1.8 Hz, 1H), 7.04-7.00 (m, 2H), 6.12 (d, J=15.3 Hz, 1H), 5.43 (d, J=14.4 Hz, 1H), 4.69 (d, J=14.4 Hz, 1H).

¹³C NMR (100 MHz, CDCl₃): δ 166.1, 158.9 (d, $J_{C-F}$=254 Hz), 156.5, 148.8, 144.1, 136.7, 135.6 (d, $J_{C-F}$=3.8 Hz), 134.9, 132.6 (d, $J_{C-F}$=14.4 Hz), 131.5 (d, $J_{CF}$=8.6 Hz), 129.9, 128.8, 128.1, 124.8, 122.6, 117.1 (d, $J_{C-F}$=3.8 Hz), 116.9, 101.9, 54.3.

[Chem. 46]

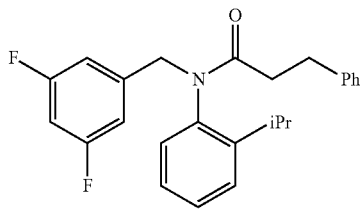

Compound 7

¹H NMR (300 MHz, CDCl₃): δ 7.37-7.16 (m, 5H), 7.01-6.99 (m, 3H), 6.74-6.66 (m, 3H), 6.36 (dd, J=7.5, 0.6 Hz, 1H), 5.47 (d, J=14.1 Hz, 1H), 3.99 (d, J=14.1 Hz, 1H), 3.05-2.84 (m, 3H), 2.38-2.12 (m, 2H), 1.15 (d, J=7.2 Hz, 3H), 1.12 (d, J=6.9 Hz, 3H).

¹³C NMR (100 MHz, CDCl₃): δ 172.9, 162.9 (dd, $J_{C-F}$=248, 12.5 Hz), 146.1, 141.3 (t, $J_{C-F}$=8.6 Hz), 141.0, 138.9, 129.3, 129.2, 128.6, 128.5, 127.5, 126.8, 126.2, 112.0 (dd, $J_{C-F}$=18.2, 6.7 Hz), 103.0 (t, $J_{C-F}$=24.9 Hz), 52.5, 36.0, 31.7, 27.6, 24.4, 23.9.

[Chem. 47]

Compound 8

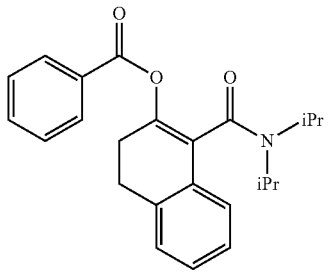

$^1$H NMR (300 MHz, CDCl$_3$): δ 8.11 (ddd, J=7.2, 1.4, 0.6 Hz, 2H), 7.63 (tt, J=7.2, 1.4 Hz, 1H), 7.46 (ddd, J=7.2, 7.2, 0.6 Hz, 1H), 7.18-7.16 (m, 3H), 7.09-7.06 (m, 1H), 4.09 (qq, J=6.6, 6.6, 6.6, 6.6 Hz, 1H), 3.38 (tt, J=6.6, 6.6 Hz, 1H), 3.21-2.97 (m, 2H), 2.81 (ddd, J=16.2, 6.7, 6.6 Hz, 1H), 2.66 (ddd, J=16.2, 11.7, 6.7 Hz, 1H), 1.57 (d, J=6.6 Hz, 3H), 1.34 (d, J=6.6 Hz, 3H), 1.01 (d, J=6.6 Hz, 3H), 0.99 (d, J=6.6 Hz, 3H).

$^{13}$C NMR (75 MHz, CDCl$_3$): δ 165.5, 164.3, 145.8, 133.6, 133.3, 131.1, 129.9, 128.9, 128.4, 127.5, 127.3, 126.6, 124.3, 124.1, 50.5, 45.6, 28.2, 25.8, 20.9, 20.8, 20.3, 20.3.

[Chem. 48]

Compound 9

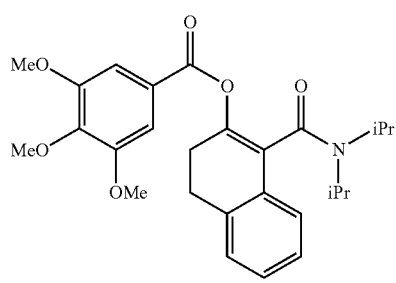

$^1$H NMR (300 MHz, CDCl$_3$): δ 7.36 (s, 2H), 7.19-7.17 (m, 3H), 7.08-7.05 (m, 1H), 4.06 (qq, J=6.6, 6.6 Hz, 1H), 3.93 (s, 3H), 3.90 (s, 6H), 3.40 (qq, J=6.9, 6.9 Hz, 1H), 3.19-2.98 (m, 2H), 2.80 (ddd, J=16.5, 7.2, 7.2 Hz, 1H), 2.62 (ddd, J=16.8, 11.4, 6.9 Hz, 1H), 1.58 (d, J=6.9 Hz, 3H), 1.39 (d, J=6.6 Hz, 3H), 1.02 (d, J=6.6 Hz, 3H), 1.00 (d, J=6.9 Hz, 3H).

$^{13}$C NMR (75 MHz, CDCl$_3$): δ 165.8, 164.2, 153.1, 146.0, 142.9, 133.6, 131.3, 127.7, 127.6, 126.9, 124.4, 124.3, 123.9, 107.3, 61.0, 56.3, 50.7, 45.8, 28.4, 26.0, 21.2, 21.0, 20.7, 20.5.

[Chem. 49]

Compound 10

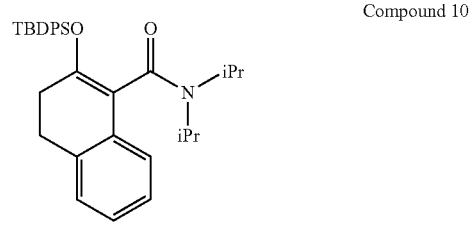

$^1$H NMR (300 MHz, CDCl$_3$): δ 7.87-7.84 (m, 2H), 7.82-7.79 (m, 2H), 7.49-7.43 (m, 3H), 7.40-7.37 (m, 3H), 7.14-7.09 (m, 1H), 7.01-6.94 (m, 3H), 4.23 (qq, J=6.6, 6.6 Hz, 1H), 3.54 (qq, J=6.9, 6.9 Hz, 1H), 2.53 (ddd, J=15.2, 10.8, 6.9 Hz, 1H), 2.38 (ddd, J=15.2, 6.9, 6.9 Hz, 1H), 2.09 (ddd, J=16.5, 6.9, 6.9 Hz, 1H), 1.92 (ddd, J=16.5, 10.8, 6.9 Hz, 1H), 1.67 (d, J=6.6 Hz, 3H), 1.65 (d, J=6.9 Hz, 3H), 1.29 (d, J=6.6 Hz, 3H), 1.04 (d, J=6.9 Hz, 3H).

$^{13}$C NMR (75 MHz, CDCl$_3$): δ 167.9, 149.9, 135.3, 135.0, 133.9, 133.5, 132.7, 131.7, 130.1, 129.9, 127.9, 126.9, 126.6, 125.2, 122.8, 116.7, 50.8, 45.7, 28.9, 28.5, 26.1, 21.7, 21.5, 20.9, 20.3, 19.3 (one aromatic carbon is overlapping).

[Chem. 50]

Compound 12

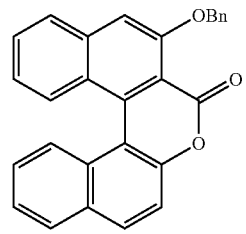

$^1$H NMR (300 MHz, CDCl$_3$): δ 8.01 (d, J=9.3 Hz, 1H), 7.91 (dd, J=8.4, 8.4 Hz, 2H), 7.79 (dd, J=9.6, 9.6 Hz, 2H), 7.70 (d, J=7.5 Hz, 2H), 7.59-7.55 (m, 2H), 7.50-7.41 (m, 4H), 7.36-7.31 (m, 2H), 7.23-7.17 (m, 1H), 5.50 (d, J=13.8 Hz, 1H), 5.44 (d, J=13.8 Hz, 1H).

$^{13}$C NMR (75 MHz, CDCl$_3$): δ 158.1, 155.5, 150.5, 138.5, 137.5, 136.7, 132.1, 131.0, 130.2, 129.7, 129.3, 128.7, 128.5, 127.8, 127.1, 127.0, 126.9, 125.9, 125.3, 124.1, 123.4, 116.9, 114.3, 112.7, 109.7, 71.1.

[Chem. 51]

Compound 13

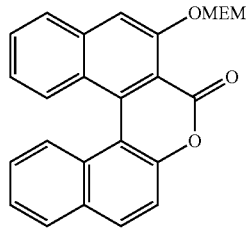

$^1$H NMR (300 MHz, CDCl$_3$): δ 8.00 (d, J=9.0 Hz, 1H), 7.93-7.85 (m, 3H), 7.77-7.74 (m, 2H), 7.62-7.57 (m, 1H), 7.56 (d, J=9.0 Hz, 1H), 7.50-7.44 (m, 1H), 7.35-7.30 (m, 1H), 7.26-7.20 (m, 1H), 5.63 (d, J=6.9 Hz, 1H), 5.60 (d, J=6.9 Hz, 1H), 4.05-4.01 (m, 2H), 3.65-3.62 (m, 2H), 3.40 (s, 3H).

$^{13}$C NMR (75 MHz, CDCl$_3$): δ 158.2, 154.0, 150.3, 138.3, 137.5, 132.1, 131.0, 130.2, 129.7, 129.2, 128.5, 127.4, 127.0, 126.0, 125.3, 124.8, 123.8, 116.9, 114.4, 113.1, 112.8, 94.8, 71.6, 68.3, 59.1.

[Chem. 52]

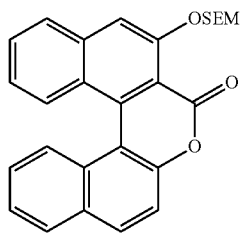

Compound 14

$^1$H NMR (300 MHz, CDCl$_3$): δ 8.00 (d, J=9.0 Hz, 1H), 7.93-7.84 (m, 3H), 7.78-7.72 (m, 2H), 7.62-7.55 (m, 2H), 7.47 (ddd, J=6.9, 6.9, 1.2 Hz, 1H), 7.32 (ddd, J=8.7, 8.7, 1.5 Hz, 1H), 7.22 (ddd, J=8.4, 8.4, 1.5 Hz, 1H), 5.59 (d, J=6.9 Hz, 1H), 5.56 (d, J=6.9 Hz, 1H), 4.03-3.88 (m, 2H), 1.07-1.01 (m, 2H), 0.19 (s, 9H).

$^{13}$C NMR (75 MHz, CDCl$_3$): δ 158.2, 154.3, 150.4, 138.3, 137.6, 132.0, 131.0, 130.2, 129.7, 129.2, 128.5, 127.4, 127.0, 126.0, 125.3, 124.6, 123.7, 116.9, 114.4, 112.8, 94.4, 67.0, 18.3, −1.3 (one aromatic carbon is overlapping).

[Chem. 53]

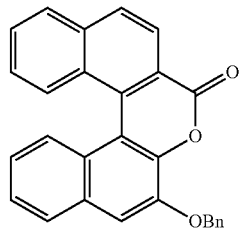

Compound 15

$^1$H NMR (300 MHz, CDCl$_3$): δ 8.39 (d, J=8.7 Hz, 1H), 8.12 (d, J=8.7 Hz, 1H), 8.06 (d, J=8.4 Hz, 1H), 8.01 (d, J=8.4 Hz, 1H), 7.81 (d, J=8.7 Hz, 1H), 7.78 (d, J=9.0 Hz, 1H), 7.68 (ddd, J=6.9, 6.9, 0.9 Hz, 1H), 7.59 (d, J=7.5 Hz, 2H), 7.47-7.35 (m, 6H), 7.22 (ddd, J=8.1, 6.6, 1.2 Hz, 1H), 5.42 (s, 2H).

$^{13}$C NMR (75 MHz, CDCl$_3$): δ 161.4, 146.2, 142.9, 136.7, 136.4, 134.9, 131.0, 129.7, 129.3, 129.1, 128.8, 128.6, 128.4, 128.2, 127.4, 127.3, 127.1, 125.8, 125.5, 124.9, 124.2, 123.5, 121.7, 114.3, 111.2, 71.1.

[Chem. 54]

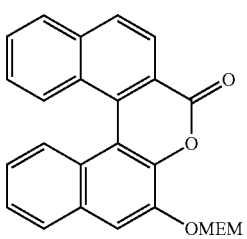

Compound 16

$^1$H NMR (300 MHz, CDCl$_3$): δ 8.37 (d, J=8.4 Hz, 1H), 8.11 (d, J=8.7 Hz, 1H), 8.06 (d, J=8.4 Hz, 1H), 8.00 (d, J=8.1 Hz, 1H), 7.86-7.80 (m, 3H), 7.68 (ddd, J=7.8, 7.8, 0.9 Hz, 1H), 7.49-7.38 (m, 2H), 7.27-7.22 (m, 1H), 5.61 (d, J=7.2 Hz, 1H), 5.57 (d, J=7.2 Hz, 1H), 4.03-4.00 (m, 2H), 3.65-3.62 (m, 2H), 3.40 (s, 3H).

$^{13}$C NMR (75 MHz, CDCl$_3$): δ 161.4, 144.8, 143.0, 136.8, 135.0, 131.1, 129.7, 129.3, 129.2, 128.7, 128.4, 127.7, 127.0, 125.9, 125.6, 125.5, 124.2, 124.0, 121.6, 114.4, 114.2, 94.7, 71.6, 68.3, 59.1.

[Chem. 55]

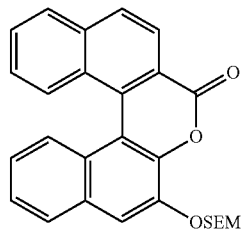

Compound 17

$^1$H NMR (300 MHz, CDCl$_3$): δ 8.38 (d, J=8.7 Hz, 1H), 8.13 (d, J=8.7 Hz, 1H), 8.06 (d, J=8.4 Hz, 1H), 8.01 (d, J=8.4 Hz, 1H), 7.85 (d, J=8.4 Hz, 1H), 7.82 (d, J=8.7 Hz, 1H), 7.79 (d, J=9.6 Hz, 1H), 7.68 (ddd, J=7.2, 7.2, 1.1 Hz, 1H), 7.49-7.30 (m, 2H), 7.27-7.20 (m, 1H), 5.57 (d, J=7.2 Hz, 1H), 5.53 (d, J=7.2 Hz, 1H), 3.96-3.87 (m, 2H), 1.07-1.01 (m, 2H), 0.02 (s, 9H).

$^{13}$C NMR (75 MHz, CDCl$_3$): δ 161.3, 144.9, 142.8, 136.6, 134.8, 131.0, 129.5, 129.2, 129.0, 128.5, 128.2, 127.5, 126.9, 125.7, 125.4, 125.2, 124.0, 123.7, 121.5, 114.1, 113.7, 94.0, 66.9, 18.2, −1.4.

[Chem. 56]

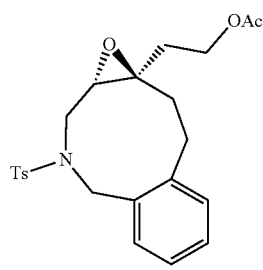

Compound 1a $^1$H NMR (300 MHz, CDCl$_3$): δ 7.80 (d, J=7.8 Hz, 1H), 7.74 (d, J=8.0 Hz, 2H), 7.37 (d, J=8.0 Hz, 2H), 7.31 (dd, J=7.4, 7.2 Hz, 1H), 7.22 (dd, J=7.8, 7.4 Hz, 1H), 7.07 (d, J=7.2 Hz, 1H), 4.82 (d, J=14.9 Hz, 1H), 4.28-4.11 (m, 2H), 3.98 (dd, J=17.1, 10.2 Hz, 1H), 3.59 (d, J=14.9 Hz, 1H), 2.85-2.70 (m, 2H), 2.59-2.50 (m, 3H), 2.47 (s, 3H), 2.12-2.03 (m, 1H), 2.04 (s, 3H), 1.26-1.15 (m, 1H), 1.01 (dd, J=12.9, 12.9 Hz, 1H).

$^{13}$C NMR (75 MHz, CDCl$_3$): δ 170.9, 143.9, 138.1, 137.8, 134.4, 131.2, 130.9, 130.1, 128.5, 127.7, 127.4, 61.0, 59.4, 57.1, 46.6, 46.1, 36.2, 29.1, 28.3, 21.7, 21.1.

[Chem. 57]

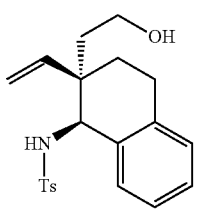

Compound 1b

¹H NMR (300 MHz, CDCl₃): δ 7.68 (d, J=8.4 Hz, 2H), 7.26 (d, J=8.4 Hz, 2H), 7.10 (dd, J=7.5, 7.1 Hz, 1H), 7.02 (d, J=7.5 Hz, 1H), 6.93 (dd, J=7.8, 7.1 Hz, 1H), 6.84 (d, J=7.8 Hz, 1H), 5.68 (dd, J=17.5, 11.1 Hz, 1H), 5.05 (d, J=11.1 Hz, 1H), 5.03 (d, J=17.5 Hz, 1H), 4.73 (d, J=8.6 Hz, 1H), 4.33 (d, J=8.6 Hz, 1H), 3.67-3.54 (m, 2H), 2.91-2.69 (m, 2H), 2.43 (s, 3H), 1.91-1.47 (m, 5H).

¹³C NMR (75 MHz, CDCl₃): δ 143.3, 142.2, 138.7, 135.4, 135.2, 129.6, 129.6, 128.8, 127.6, 127.2, 126.2, 115.6, 59.4, 59.4, 42.2, 37.5, 25.2, 25.1, 21.6.

[Chem. 58]

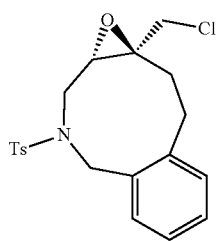

Compound 2a

¹H NMR (300 MHz, CDCl₃): δ 7.79 (d, J=7.8 Hz, 1H), 7.72 (d, J=8.1 Hz, 2H), 7.37 (d, J=8.1 Hz, 2H), 7.32 (dd, J=7.8, 7.4 Hz, 1H), 7.23 (dd, J=7.8, 7.8 Hz, 1H), 7.08 (d, J=7.4 Hz, 1H), 4.85 (d, J=14.6 Hz, 1H), 4.04 (dd, J=11.1, 2.7 Hz, 1H), 3.80 (d, J=11.6 Hz, 1H), 3.47 (d, J=14.6 Hz, 1H), 3.04 (d, J=11.6 Hz, 1H), 2.84-2.70 (m, 4H), 2.53 (dd, J=11.1, 11.1 Hz, 1H), 2.47 (s, 3H), 1.02 (dd, J=10.8, 10.2 Hz, 1H).

¹³C NMR (75 MHz, CDCl₃): δ 144.2, 137.9, 137.4, 134.1, 131.2, 130.9, 130.1, 128.7, 127.8, 127.4, 60.1, 59.3, 47.0, 46.1, 44.5, 33.5, 29.2, 21.7.

[Chem. 59]

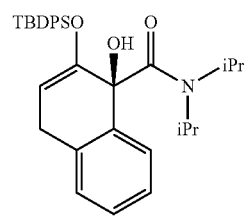

Compound 10b

¹H NMR (300 MHz, CDCl₃): δ 7.90-7.87 (m, 2H), 7.83-7.80 (m, 2H), 7.45-7.34 (m, 6H), 7.22-7.17 (m, 3H), 7.17-7.08 (m, 1H), 6.62 (s, 1H), 4.82 (dd, J=4.0, 4.0 Hz, 1H), 4.03 (tt, J=6.6, 6.6 Hz, 1H), 3.40 (dd, J=22.5, 4.0 Hz, 1H), 3.35 (tt, J=6.6, 6.6 Hz, 1H), 3.20 (dd, J=22.5, 4.0 Hz, 1H), 1.54 (d, J=6.6 Hz, 3H), 1.45 (d, J=6.6 Hz, 3H), 1.09 (d, J=6.6 Hz, 3H), 0.26 (d, J=6.6 Hz, 3H).

¹³C NMR (75 MHz, CDCl₃): δ 170.9, 148.7, 137.4, 136.1, 135.6, 134.0, 132.9, 131.6, 129.80, 129.76, 127.9, 127.7, 127.6, 127.5, 127.4, 126.8, 103.2, 73.1, 48.5, 47.1, 28.9, 26.5, 20.6, 20.2, 19.7, 18.3 (one aliphatic carbon is overlapping).

[Chem. 60]

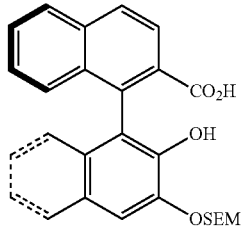

Compound 17a

¹H NMR (300 MHz, CDCl₃): δ 8.15 (d, J=8.4 Hz, 1H), 8.03 (d, J=8.7 Hz, 1H), 7.96 (d, J=8.1 Hz, 1H), 7.77 (d, J=7.8 Hz, 1H), 7.61 (s, 1H), 7.54 (ddd, J=6.9, 6.9, 1.5 Hz, 1H), 7.41 (d, J=8.4 Hz, 1H), 7.35-7.26 (m, 2H), 7.12 (ddd, J=7.2, 7.2, 1.2 Hz, 1H), 6.94 (d, J=8.1 Hz, 1H), 5.95 (s, 1H), 5.49 (s, 2H), 3.94-3.85 (m, 4H), 1.08-1.02 (m, 2H), 0.72 (dd, J=6.9, 6.9 Hz, 3H), 0.04 (s, 9H).

¹³C NMR (75 MHz, CDCl₃): δ 167.8, 145.0, 143.0, 135.3, 135.2, 132.7, 130.1, 129.7, 128.7, 128.4, 128.2, 127.8, 127.5, 127.1, 126.9, 126.3, 124.8, 124.7, 123.9, 119.2, 109.9, 94.4, 67.2, 60.6, 18.3, 13.4, −1.3.

INDUSTRIAL APPLICABILITY

According to the method for producing an optically active substance according to an embodiment of the present invention, one enantiomer of a chiral molecule can be selectively and efficiently obtained by a simple operation without using a chiral reagent. The chiral molecule whose enantiomer has been thus obtained has extremely high optical activity and can be effectively used as pharmaceuticals and functional materials. Thus, the present invention has high industrial applicability.

The invention claimed is:

1. A method for producing an optically active substance, the method comprising an asymmetric induction, wherein an asymmetry inducer is allowed to act on a chiral molecule having a half-life of enantiomeric excess of shorter than 10 hours at 50° C., thereby increasing abundance of one enantiomer of the chiral molecule, wherein:

the chiral molecule is represented by any of General Formulas (1) to (3), (4a), (4b), (7) and (8) below:

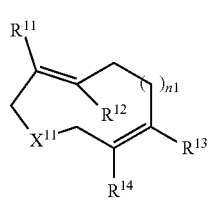

(1)

in General Formula (1), $R^{11}$ to $R^{14}$ each independently represent a hydrogen atom or a substituent; $X^{11}$ represents O, S, or $NR^{15}$, where $R^{15}$ represents a substituent; and n1 represents an integer from 1 to 10;

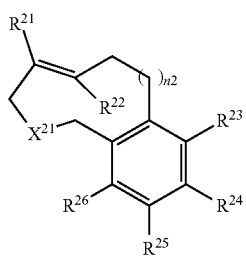
(2)

in General Formula (2), $R^{21}$ and $R^{22}$ each independently represent a hydrogen atom or a substituent; $R^{23}$ to $R^{26}$ each independently represent a hydrogen atom or a substituent; $X^{21}$ represents O, S, or $NR^{27}$, where $R^{27}$ represents a substituent; and n2 represents an integer from 1 to 10;

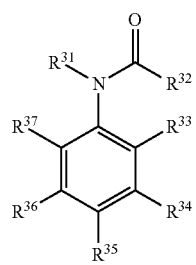
(3)

in General Formula (3), $R^{31}$ and $R^{32}$ each independently represent a substituent, and $R^{33}$ to $R^{37}$ each independently represent a hydrogen atom or a substituent;

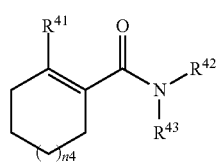
(4a)

in General Formula (4a), $R^{41}$ to $R^{43}$ each independently represent a substituent; n4 represents an integer from 1 to 10; and a benzene ring is fused in place of any —CH$_2$CH$_2$— constituting the cycloalkylene ring of General Formula (4a) or no benzene ring is fused to the cycloalkene ring;

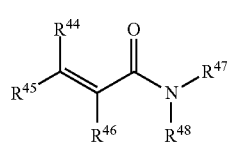
(4b)

in General Formula (4b), $R^{44}$ to $R^{48}$ each independently represent a substituent;

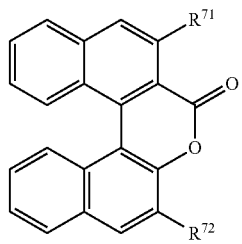
(7)

in General Formula (7), $R^{71}$ and $R^{72}$ each independently represent a hydrogen atom or a substituent;

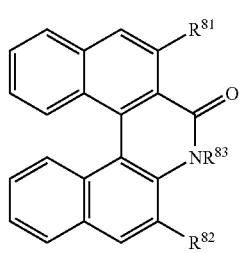
(8)

in General Formula (8), $R^{81}$ and $R^{82}$ each independently represent a hydrogen atom or a substituent; and $R^{83}$ represents a substituent, all of said substituents are independently selected from the group consisting of a hydroxy group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, a diarylamino group having from 12 to 40 carbon atoms, a substituted or unsubstituted carbazolyl group having from 12 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group; and the asymmetry inducer is a sugar chain derivative including a structure in which a phenyl group is linked to a cellulose or an amylose via an ester group or a urethane group.

2. The method for producing an optically active substance according to claim 1, wherein the asymmetry inducer is allowed to act on the chiral molecule, thereby increasing abundance of one enantiomer without cleavage or reformation of a bond in the chiral molecule.

3. The method for producing an optically active substance according to claim 1, wherein one enantiomer and the other enantiomer of the chiral molecule differ from each other in conformation.

4. The method for producing an optically active substance according to claim 2, wherein the chiral molecule is a planarly asymmetric molecule.

5. The method for producing an optically active substance according to claim 2, wherein the chiral molecule is an axially asymmetric molecule, with the proviso that a substituted biphenyl molecule is excluded.

6. The method for producing an optically active substance according to claim 2, wherein the chiral molecule is a helically asymmetric molecule.

7. The method for producing an optically active substance according to claim 1, the method further comprising an isolation, wherein the one enantiomer is isolated after the asymmetric induction.

8. The method for producing an optically active substance according to claim 1, the method further comprising an asymmetric stabilization, wherein a reagent is allowed to act on the chiral molecule after the asymmetric induction, thereby converting the one enantiomer to one enantiomer of a second chiral molecule having a longer half-life of enantiomeric excess than that of the chiral molecule, wherein the reagent is an epoxidizing agent, an alkyllithium reagent, an alkylmagnesium reagent, or a metal alkoxide reagent.

9. A method for producing a chiral molecule, the method comprising an asymmetric stabilization, wherein a reagent is allowed to act on an optically active substance of a first chiral molecule having a half-life of enantiomeric excess of shorter than 10 hours at 50° C., of which one enantiomer is present in excess over the other enantiomer, thereby converting the optically active substance of the first chiral molecule to an optically active substance of a second chiral molecule having a longer half-life of enantiomeric excess, wherein:
the first chiral molecule is represented by any of General Formulas (2) to (3), (4a), (4b), (7) and (8) below:

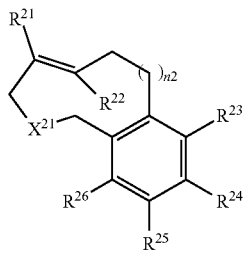

(2)

in General Formula (2), $R^{21}$ and $R^{22}$ each independently represent a hydrogen atom or a substituent; $R^{23}$ to $R^{26}$ each independently represent a hydrogen atom or a substituent; $X^{21}$ represents O, S, or $NR^{27}$, where $R^{27}$ represents a substituent; and n2 represents an integer from 1 to 10;

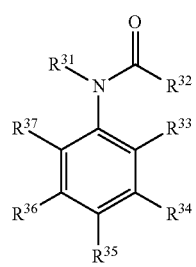

(3)

in General Formula (3), $R^{31}$ and $R^{32}$ each independently represent a substituent, and $R^{33}$ to $R^{37}$ each independently represent a hydrogen atom or a substituent;

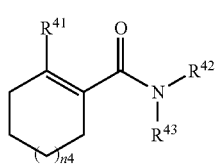

(4a)

in General Formula (4a), $R^{41}$ to $R^{43}$ each independently represent a substituent; n4 represents an integer from 1 to 10; and a benzene ring is fused in place of any —$CH_2CH_2$— constituting the cycloalkylene ring of General Formula (4a) or no benzene ring is fused to the cycloalkene ring;

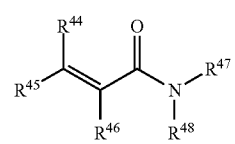

(4b)

in General Formula (4b), $R^{44}$ to $R^{48}$ each independently represent a substituent;

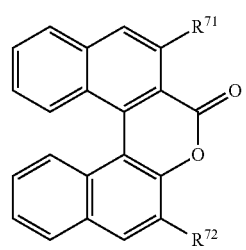

(7)

in General Formula (7), $R^{71}$ and $R^{72}$ each independently represent a hydrogen atom or a substituent;

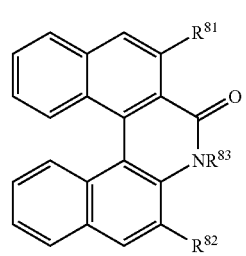

(8)

in General Formula (8), $R^{81}$ and $R^{82}$ each independently represent a hydrogen atom or a substituent; and $R^{83}$ represents a substituent,
all of said substituents are independently selected from the group consisting of a hydroxy group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, a diarylamino group having from 12 to 40 carbon atoms, a substituted or unsubstituted carbazolyl group having from 12 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group; and the reagent is an epoxidizing agent, an alkyllithium reagent, an alkylmagnesium reagent, or a metal alkoxide reagent.

10. A method for producing a chiral molecule, the method comprising:

an asymmetric stabilization, wherein a reagent is allowed to act on an optically active substance of a first chiral molecule having a half-life of enantiomeric excess of shorter than 10 hours at 50° C., of which one enantiomer is present in excess over the other enantiomer, thereby converting the optically active substance of the first chiral molecule to an optically active substance of a second chiral molecule having a longer half-life of enantiomeric excess, allowing an asymmetry inducer to act on a chiral molecule having a half-life of enantiomeric excess of shorter than 10 hours at 50° C. before the asymmetric stabilization, thereby increasing abundance of one enantiomer of the chiral molecule to obtain the first chiral molecule, of which one enantiomer of the chiral molecule is present in excess over the other enantiomer of the chiral molecule, wherein the chiral molecule and the first chiral molecule are represented by any of General Formulas (1) to (3), (4a), (4b), (7) and (8) below:

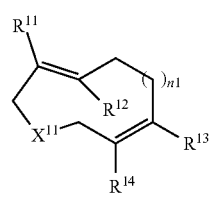
(1)

in General Formula (1), $R^{11}$ to $R^{14}$ each independently represent a hydrogen atom or a substituent; $X^{11}$ represents O, S, or $NR^{15}$, where $R^{15}$ represents a substituent; and n1 represents an integer from 1 to 10;

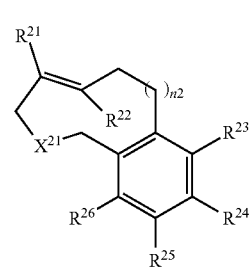
(2)

in General Formula (2), $R^{21}$ and $R^{22}$ each independently represent a hydrogen atom or a substituent; $R^{23}$ to $R^{26}$ each independently represent a hydrogen atom or a substituent; $X^{21}$ represents O, S, or $NR^{27}$, where $R^{27}$ represents a substituent; and n2 represents an integer from 1 to 10;

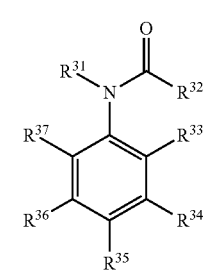
(3)

in General Formula (3), $R^{31}$ and $R^{32}$ each independently represent a substituent, and $R^{33}$ to $R^{37}$ each independently represent a hydrogen atom or a substituent;

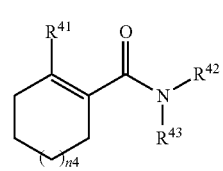
(4a)

in General Formula (4a), $R^{41}$ to $R^{43}$ each independently represent a substituent; n4 represents an integer from 1 to 10; and a benzene ring is fused in place of any —CH$_2$CH$_2$— constituting the cycloalkylene ring of General Formula (4a) or no benzene ring is fused to the cycloalkene ring;

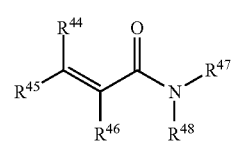
(4b)

in General Formula (4b), $R^{44}$ to $R^{48}$ each independently represent a substituent;

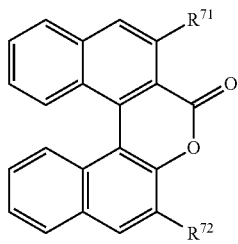

in General Formula (7), $R^{71}$ and $R^{72}$ each independently represent a hydrogen atom or a substituent;

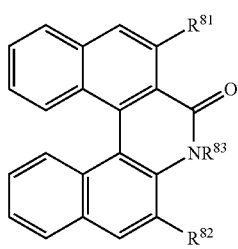

in General Formula (8), $R^{81}$ and $R^{82}$ each independently represent a hydrogen atom or a substituent; and $R^{83}$ represents a substituent, all of said substituents are independently selected from the group consisting of a hydroxy group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, a diarylamino group having from 12 to 40 carbon atoms, a substituted or unsubstituted carbazolyl group having from 12 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group;

the reagent is an epoxidizing agent, an alkyllithium reagent, an alkylmagnesium reagent, or a metal alkoxide reagent; and the asymmetry inducer is a sugar chain derivative including a structure in which a phenyl group is linked to a cellulose or an amylose via an ester group or a urethane group.

* * * * *